United States Patent
Sherman

(10) Patent No.: US 6,488,678 B2
(45) Date of Patent: Dec. 3, 2002

(54) RF ABLATION APPARATUS AND METHOD USING UNIPOLAR AND BIPOLAR TECHNIQUES

(75) Inventor: Marshall L. Sherman, Cardiff, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 3 days.

(21) Appl. No.: 09/758,636

(22) Filed: Jan. 10, 2001

(65) Prior Publication Data
US 2001/0008967 A1 Jul. 19, 2001

Related U.S. Application Data

(60) Continuation of application No. 09/501,472, filed on Feb. 9, 2000, now Pat. No. 6,200,314, which is a division of application No. 09/073,392, filed on May 5, 1998, now Pat. No. 6,059,778.

(51) Int. Cl.$^7$ ............................................... A01B 18/18
(52) U.S. Cl. ............................... 606/34; 606/35; 606/41; 606/42; 606/50
(58) Field of Search ............................... 606/32, 34, 35, 606/38, 41–50; 607/96–101, 122, 150

(56) References Cited

U.S. PATENT DOCUMENTS

| | | | |
|---|---|---|---|
| 4,281,373 A | 7/1981 | Mabille | 363/21 |
| 4,559,943 A | 12/1985 | Bowers | 128/303 |
| 4,739,759 A | 4/1988 | Rexroth et al. | 128/303 |
| 4,907,589 A | 3/1990 | Cosman | 606/34 |
| 4,936,281 A | 6/1990 | Stasz | 128/660.03 |
| 5,300,068 A | 4/1994 | Rosar et al. | 606/34 |
| 5,372,596 A | * 12/1994 | Klicek et al. | 606/35 |
| 5,383,917 A | 1/1995 | Desai et al. | 607/702 |
| 5,437,664 A | 8/1995 | Cohen et al. | 606/42 |
| 5,438,302 A | 8/1995 | Goble | 331/167 |
| 5,476,495 A | 12/1995 | Kordis et al. | 607/122 |
| 5,487,385 A | 1/1996 | Avitall | 128/642 |
| 5,496,312 A | 3/1996 | Klicek | 606/34 |
| 5,500,011 A | 3/1996 | Desai | 607/116 |
| 5,514,130 A | 5/1996 | Baker | 606/41 |
| 5,540,681 A | 7/1996 | Strul et al. | 606/34 |
| 5,542,916 A | 8/1996 | Hirsch et al. | 604/22 |
| 5,562,720 A | 10/1996 | Stern et al. | |
| 5,582,609 A | 12/1996 | Swanson et al. | 606/39 |
| 5,584,830 A | * 12/1996 | Ladd et al. | 606/34 |
| 5,617,854 A | 4/1997 | Munsif | 128/642 |
| 5,620,481 A | 4/1997 | Desai et al. | 607/101 |
| 5,643,197 A | 7/1997 | Brucker et al. | 604/20 |
| 5,697,928 A | 12/1997 | Walcott et al. | 606/41 |

(List continued on next page.)

FOREIGN PATENT DOCUMENTS

| | | |
|---|---|---|
| WO | WO93/00958 | 1/1993 |
| WO | WO96/00036 | 1/1996 |

*Primary Examiner*—Michael Peffley
*Assistant Examiner*—David M. Ruddy
(74) *Attorney, Agent, or Firm*—Fulwider Patton Lee & Utecht, LLP

(57) ABSTRACT

An apparatus for delivering energy to a biological site includes an electrode device having a plurality of electrodes, the electrode device positioned proximal the biological site. A power control system supplies power having a controllable phase angle to each of the electrodes. A backplate is also positioned proximal the biological site so that the biological site is interposed between the electrode device and the backplate. The backplate is maintained at the reference voltage level in relation to the power. The power control system controls the phase angle of the power so that the current flow between the electrodes and between the electrodes and the backplate results in the continuity and depth of lesions desired. In a preferred embodiment, the electrodes are arranged in a substantially linear array.

38 Claims, 15 Drawing Sheets

U.S. PATENT DOCUMENTS

| | | | |
|---|---|---|---|
| 5,769,847 A | | 6/1998 | Panescu et al. ............... 606/42 |
| 5,797,903 A | * | 8/1998 | Swanson et al. |
| 5,810,802 A | | 9/1998 | Panescu et al. ............... 606/31 |
| 5,827,273 A | * | 10/1998 | Edwards ..................... 606/41 |
| 6,113,596 A | | 9/2000 | Hooven et al. |
| 6,139,546 A | | 10/2000 | Koenig et al. |
| 6,142,992 A | | 11/2000 | Cheng et al. |
| 6,146,379 A | | 11/2000 | Fleischman et al. |
| 6,293,941 B1 | * | 9/2001 | Stral et al. .................... 606/34 |
| 6,309,386 B1 | * | 10/2001 | Bek ............................ 606/34 |

\* cited by examiner

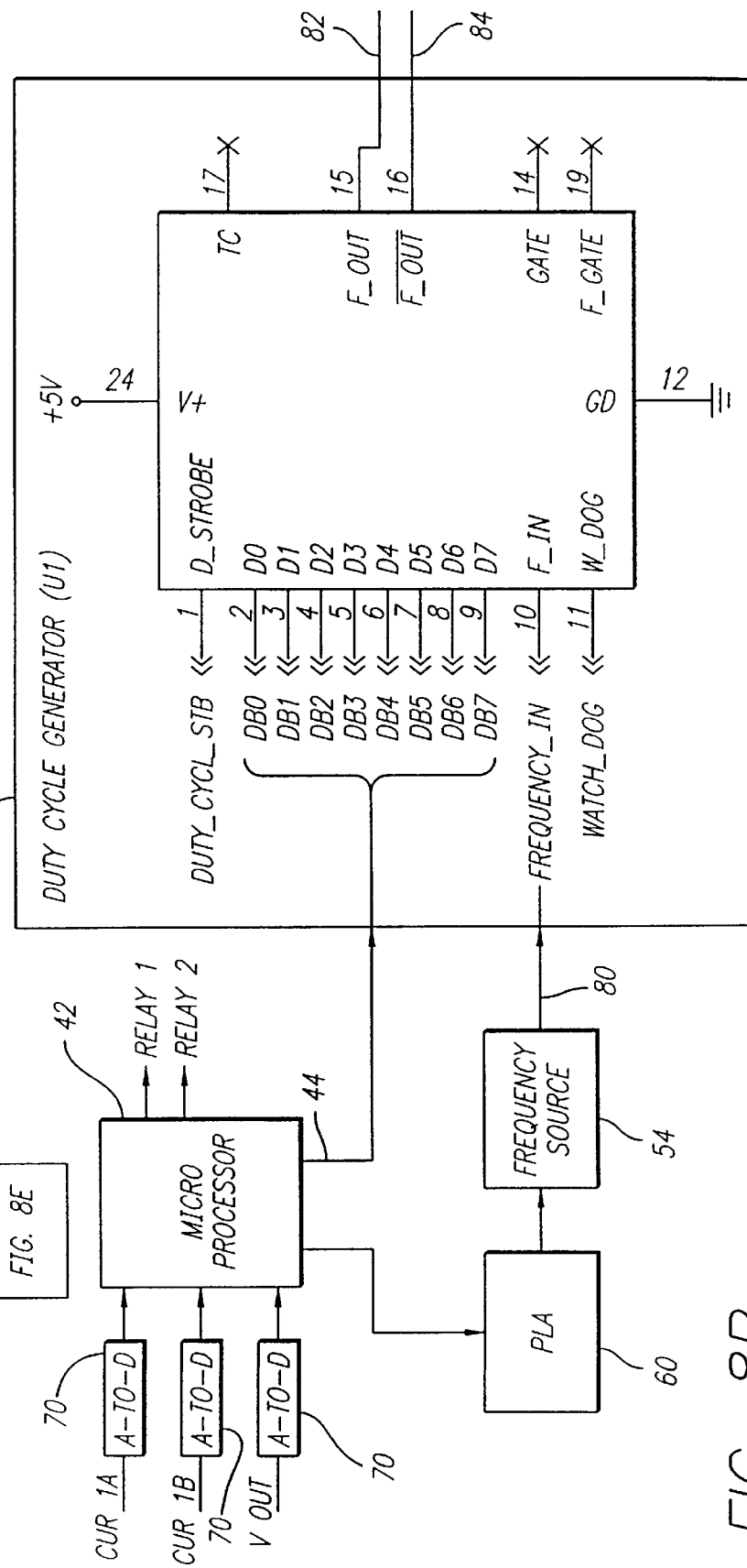

RF ABLATION APPARATUS AND METHOD USING UNIPOLAR AND BIPOLAR TECHNIQUES

RELATED APPLICATIONS

This is a continuation of application Ser. No. 09/501,472; filed Feb. 9, 2000, now U.S. Pat. No. 6,200,314, which is a division of application Ser. No. 09/073,392; filed May 5, 1998, now U.S. Pat. No. 6,059,778.

BACKGROUND OF THE INVENTION

The invention relates generally to an electrophysiological ("EP") apparatus and method for providing energy to biological tissue, and more particularly, to a radio frequency ("RF") ablation apparatus for controlling the flow of current through a biological site so that the volume of ablation lesions may be controlled.

The heart beat in a healthy human is controlled by the sinoatrial node ("S-A node") located in the wall of the right atrium. The S-A node generates electrical signal potentials that are transmitted through pathways of conductive heart tissue in the atrium to the atrioventricular node ("A-V node") which in turn transmits the electrical signals throughout the ventricle by means of the His and Purkinje conductive tissues. Improper growth of, or damage to, the conductive tissue in the heart can interfere with the passage of regular electrical signals from the S-A and A-V nodes. Electrical signal irregularities resulting from such interference can disturb the normal rhythm of the heart and cause an abnormal rhythmic condition referred to as "cardiac arrhythmia."

While there are different treatments for cardiac arrhythmia, including the application of anti-arrhythmia drugs, in many cases ablation of the damaged tissue can restore the correct operation of the heart. Such ablation can be performed by percutaneous ablation, a procedure in which a catheter is percutaneously introduced into the patient and directed through an artery to the atrium or ventricle of the heart to perform single or multiple diagnostic, therapeutic, and/or surgical procedures. In such case, an ablation procedure is used to destroy the tissue causing the arrhythmia in an attempt to remove the electrical signal irregularities or create a conductive tissue block to restore normal heart beat or at least an improved heart beat. Successful ablation of the conductive tissue at the arrhythmia initiation site usually terminates the arrhythmia or at least moderates the heart rhythm to acceptable levels. A widely accepted treatment for arrhythmia involves the application of RF energy to the conductive tissue.

In the case of atrial fibrillation ("AF"), a procedure published by Cox et al. and known as the "Maze procedure" involves continuous atrial incisions to prevent atrial reentry and to allow sinus impulses to activate the entire myocardium. While this procedure has been found to be successful, it involves an intensely invasive approach. It is more desirable to accomplish the same result as the Maze procedure by use of a less invasive approach, such as through the use of an appropriate EP catheter system.

There are two general methods of applying RF energy to cardiac tissue, unipolar and bipolar. In the unipolar method a large surface area electrode; e.g., a backplate, is placed on the chest, back or other external location of the patient to serve as a return. The backplate completes an electrical circuit with one or more electrodes that are introduced into the heart, usually via a catheter, and placed in intimate contact with the aberrant conductive tissue. In the bipolar method, electrodes introduced into the heart have different potentials and complete an electrical circuit between themselves. In the bipolar method, the flux traveling between the two electrodes of the catheter enters the tissue to cause ablation.

During ablation, the electrodes are placed in intimate contact with the target endocardial tissue. RF energy is applied to the electrodes to raise the temperature of the target tissue to a non-viable state. In general, the temperature boundary between viable and non-viable tissue is approximately 48° Centigrade. Tissue heated to a temperature above 48° C. becomes non-viable and defines the ablation volume. The objective is to elevate the tissue temperature, which is generally at 37° C., fairly uniformly to an ablation temperature above 48° C., while keeping both the temperature at the tissue surface and the temperature of the electrode below 100° C.

A basic configuration of an ablation catheter for applying RF energy includes a distal tip which is fitted with an electrode device. The electrode device is the source of an electrical signal that causes heating of the contacting and neighboring tissue. In the unipolar method, the electrode device may include a single electrode used for emitting RF energy. This single electrode acts as one electrical pole. The other electrical pole is formed by the backplate in contact with a patient's external body part. A RF source is applied to the electrode. The RF source is typically in the 500 kHz region and produces a sinusoidal voltage. When this is delivered between the distal tip of a standard electrode catheter and a backplate, it produces a localized RF heating effect and produces a well defined, deep acute lesion slightly larger than the tip electrode.

In some procedures a lesion having a larger surface area than that produced by a single electrode in a unipolar arrangement may be required. To this end numerous ablation catheters have been designed. In one catheter designed to provide a larger surface ablation area, an electrode device having four peripheral electrodes which extend from a retracted mode is used. See U.S. Pat. No. 5,500,011 to Desai. When extended, i.e., fanned out, the four peripheral electrodes and the central electrode form an electrode array that covers a larger surface area of the tissue than a single electrode. When used with a conventional RF power source, and in conjunction with a backplate, the five electrodes produce five lesion spots distributed over the area spanned by the electrode array. The lesions produced are discontinuous in relation to each other and there are areas between the electrodes that remain unablated. This device must be manipulated so that when expanded, all electrodes are in contact with the endocardium. An "end on" approach is required such that the end of the catheter, on which all five electrodes are mounted, is in intimate contact with the target tissue.

In another catheter an electrode device having a central electrode and a number of peripheral electrodes which also fan out from a retracted mode is used. During ablation a backplate is not used; instead the central electrode functions as the reference while the peripheral electrodes have multiphase RF power applied to them. For example, see U.S. Pat. No. 5,383,917 to Desai et al. While this technique provides a more continuous lesion covering a larger surface area of the tissue, the ablation volume is relatively shallow with a nonuniform depth of the lesion. This arrangement also requires the same manipulation of the catheter such that an end-on contact is made by the expanded electrodes, as discussed above. Lesions having a non-uniform ablation volume are undesirable as the depth at one part of the lesion may not be sufficient to stop the irregular signal pathways. Arrhythmia may reoccur because the irregular signals may pass under such an ablation volume and the procedure must then be repeated to once again attempt to obtain an ablation volume having sufficient depth.

The mechanical configuration of both of the above-described techniques comprises an expanding approach. When used for ablation, an electrode device is typically part of a catheter system. Accordingly, it is desirable to minimize the diameter of the electrode device during introduction to and withdrawal from the patient to lessen trauma to the patient. Therefore, electrode devices having peripheral expandable electrodes must be configured so that the peripheral electrodes are expandable to a large size yet are retractable to as small a size as practical. Such requirements pose design and manufacturing difficulties due to the movement of mechanical parts required for proper operation. Further considerations are the undesirable complexity and increased manufacturing cost associated with an expandable a catheter.

Hence, those skilled in the art have recognized a need for a structurally stable invasive ablation apparatus and method that are capable of controlling the flow of current through a biological site so that lesions with controllable surface and depth characteristics may be produced and the ablation volume thereby controlled. The invention fulfills these needs and others.

SUMMARY OF THE INVENTION

Briefly, and in general terms, the invention is directed to an apparatus and a method for controlling the application of energy to a biological site during ablation to thereby control the surface area, the continuity, and the depth of lesion produced during ablation.

In one aspect, the invention is directed to an apparatus for delivering energy to a biological site comprising a catheter having a plurality of electrodes at its distal end. The distal end is positionable so that the electrodes are located at the biological site. The apparatus also includes a backplate positionable proximal the biological site so that the biological site is interposed between the electrodes and the backplate and a power control system providing power to each of the electrodes, the power having a duty cycle with an on period and an off period. During the on period of the duty cycle, the power is selected such that at least two electrodes have voltage levels that differ from each other and at least one electrode has a voltage level that differs from the backplate so that current flows between the two electrodes and between at least one electrode and the backplate. During the off period of the duty cycle, the power is selected such that each electrode and the backplate have substantially the same voltage levels so that substantially no current flows between the electrodes and between the electrodes and the backplate.

In more detailed aspects, the power control system provides separate power to each of the plurality of electrodes with the power to each electrode being individually controllable as to duty cycle. In another detailed aspect, the power control system controls the duty cycle of the power to be approximately ten percent. In a further detailed aspect, a temperature sensing device is located at least one of the electrodes for providing a temperature signal to the power control system representative of the temperature at the electrode. The power control system controls the duty cycle of the power in response to the temperature signal. In another detailed aspect, the apparatus includes a measurement device that senses at least one characteristic of the power applied to at least one electrode and provides a power measurement signal and the power control system receives the power measurement signal and determines an impedance measurement based on the power measurement signal and controls the duty cycle of the power in response to the power measurement signal.

In another aspect, an apparatus for delivering energy to heart tissue comprises a catheter having at least three electrodes arranged in a linear array at its distal end. The distal end is positionable so that the electrodes are located at the heart tissue. The apparatus also includes a backplate positionable so that the heart tissue is interposed between the electrodes and the backplate, a power control system providing power to each of the electrodes, the power having a duty cycle with an on period and an off period. During the on period of the duty cycle, at least two of the electrodes have different phase angles and the power applied to at least one electrode has a voltage level that differs from the backplate so that current flows between said two electrodes and at least one electrode and the backplate. During the off period of the duty cycle, the power is selected such that each electrode and the backplate have substantially the same voltage levels so that substantially no current flows between the electrodes and between the electrodes and the backplate.

In yet another aspect, a method for delivering energy to a biological site comprises the steps of positioning a catheter having a plurality of electrodes at its distal end at the biological site; positioning a backplate proximal the biological site so that the biological site is interposed between the electrode device and the backplate; and providing power to each of the electrodes, the power having a duty cycle with an on period and an off period. The method also includes the steps of, during the on period of the duty cycle, selecting the power such that at least two electrodes have voltage levels that differ from each other and at least one electrode has a voltage level that differs from the backplate so that current flows between the two electrodes and between at least one electrode and the backplate; and during the off period of the duty cycle, terminating the power such that substantially no current flows between the electrodes and between the electrodes and the backplate.

These and other aspects and advantages of the present invention will become apparent from the following more detailed description, when taken in conjunction with the accompanying drawings which illustrate, by way of example, the preferred embodiments of the invention.

BRIEF DESCRIPTION OF THE DRAWINGS

FIGS. 2-1 and 2-2 form block diagram presenting more detail of a power control system in accordance with aspects of the invention, showing phase angle control, duty cycle control, and impedance and temperature monitoring;

FIGS. 8A, 8B, 8C, 8D, and 8E are schematic diagrams of an embodiment of a power control system in accordance with aspects of the invention with FIG. 8A showing how FIGS. 8B, 8C, 8D and 8E are related;

DETAILED DESCRIPTION OF THE PREFERRED EMBODIMENTS

Figure 1:
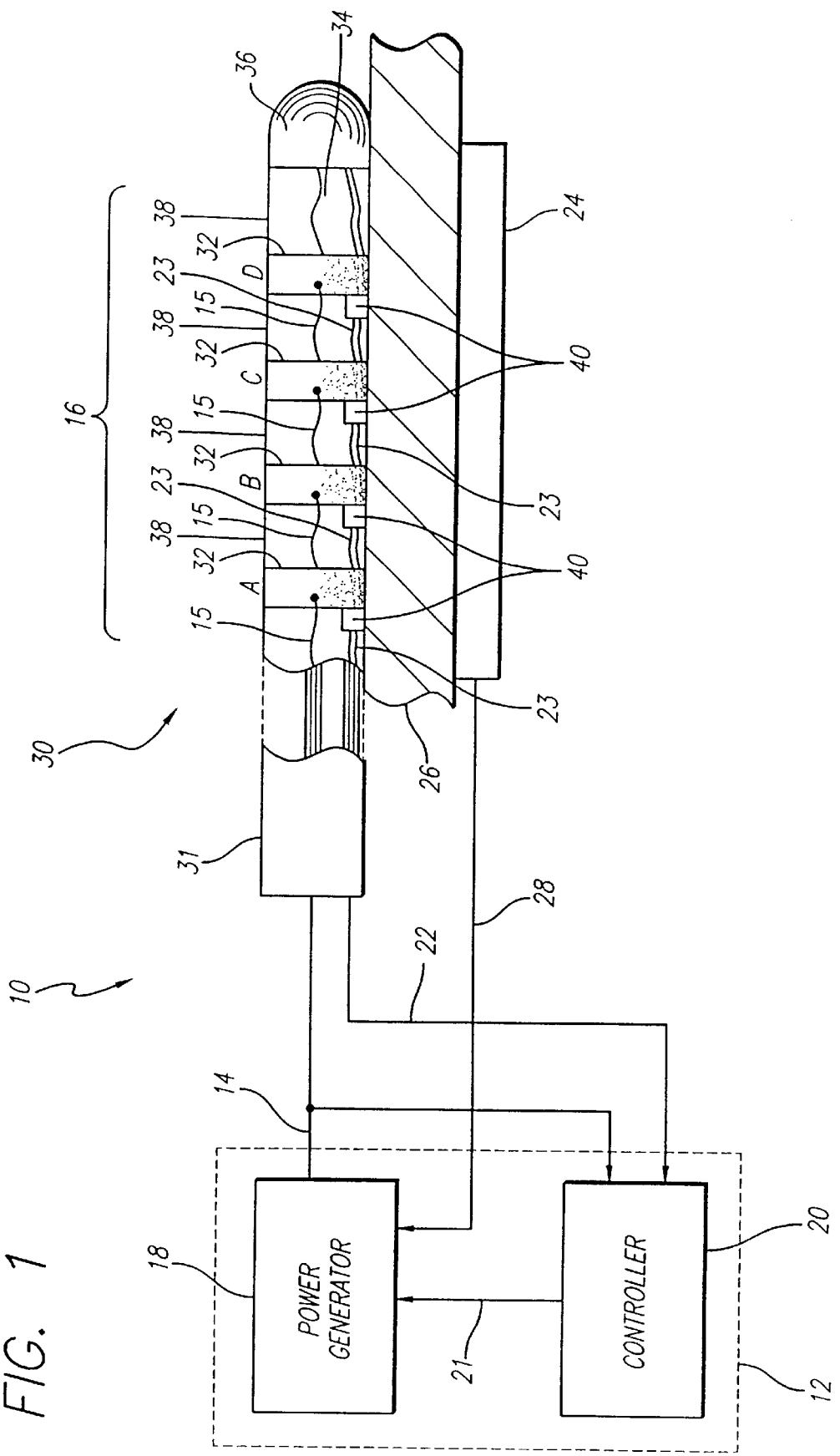
FIG. 1 is a schematic diagram of an ablation apparatus including a power control system, electrode device and backplate.

Turning now to the drawings, in which like reference numerals are used to designate like or corresponding elements among the several figures, in FIG. 1 there is shown an ablation apparatus 10 in accordance with aspects of the present invention. The apparatus 10 includes a power control system 12 that provides power or drive 14 to an electrode device 16. The power control system 12 comprises a power generator 18 that may have any number of output channels through which it provides the power 14. The operation of the power generator 18 is controlled by a controller 20 which outputs control signals 21 to the power generator 18. The controller 20 monitors the power 14 provided by the power generator 18. In addition, the controller 20 also receives temperature signals 22 from the electrode device 16. Based on the power 14 and temperature signals 22 the controller 20 adjusts the operation of the power generator 18. A backplate 24 is located proximal to the biological site 26 opposite the site from the electrode device 16, and is connected by a backplate wire 28 to the power generator 18. The backplate 24 is set at the reference level to the power provided to the electrodes, as discussed in detail below.

The electrode device 16 is typically part of a steerable EP catheter 30 capable of being percutaneously introduced into a biological site 26, e.g., the atrium or ventricle of the heart. The electrode device 16 is shown in schematic form with the components drawn to more clearly illustrate the relationship between the components and the relationship between the components and the power control system 12. In this embodiment, the catheter 30 comprises a distal segment 34 and a handle 31 located outside the patient. A preferred embodiment of the electrode device 16 includes twelve band electrodes 32 arranged in a substantially linear array along the distal segment 34 of the catheter 30. The electrode device 16 may include a tip electrode 36. (For clarity of illustration, only four band electrodes 32 are shown in the figures although as stated, a preferred embodiment may include many more.) The band electrodes 32 are arranged so that there is space 38 between adjacent electrodes. In one configuration of the electrode device 16, the width of the band electrodes 32 is 3 mm and the space 38 between the electrodes is 4 mm. The total length of the electrode device 16, as such, is approximately 8 cm.

The arrangement of the band electrodes 32 is not limited to a linear array and may take the form of other patterns. A substantially linear array is preferred for certain therapeutic procedures, such as treatment of atrial fibrillation, in which linear lesions of typically 4 to 8 cm in length are desired. A linear array is more easily carried by the catheter 30 and also lessens the size of the catheter.

The band electrodes 32 are formed of a material having a significantly higher thermal conductivity than that of the biological tissue 26. Possible materials include silver, copper, gold, chromium, aluminum, molybdenum, tungsten, nickel, platinum, and platinum/10% iridium. Because of the difference in thermal conductivity between the electrodes 32 and the tissue 26, the electrodes 32 cool off more rapidly in the flowing fluids at the biological site. The power supplied to the electrodes 32 may be adjusted during ablation to allow for the cooling of the electrodes while at the same time allowing for the temperature of the tissue to build up so that ablation results. The electrodes 32 are sized so that the surface area available for contact with fluid in the heart, e.g., blood, is sufficient to allow for efficient heat dissipation from the electrodes to the surrounding blood. In a preferred embodiment, the electrodes 32 are 7 French (2.3 mm in diameter) with a length of 3 mm.

The thickness of the band electrodes 32 also affects the ability of the electrode to draw thermal energy away from the tissue it contacts. In the present embodiment, the electrodes 32 are kept substantially thin so that the electrodes effectively draw energy away from the tissue without having to unduly increase the outer diameter of the electrode. In a preferred embodiment of the invention, the thickness of the band electrodes is 0.05 to 0.13 mm (0.002 to 0.005 inches).

Associated with the electrode device 16 are temperature sensors 40 for monitoring the temperature of the electrode device 16 at various points along its length. In one embodiment, each band electrode 32 has a temperature sensor 40 mounted to it. Each temperature sensor 40 provides a temperature signal 22 to the controller 20 which is indicative of the temperature of the respective band electrode 32 at that sensor. In another embodiment of the electrode device 16 a temperature sensor 40 is mounted on every other band electrode 32. Thus for a catheter having twelve electrodes, there are temperature sensors on six electrodes. In yet another embodiment of the electrode device 16 every other electrode has two temperature sensors 40. In FIG. 1, which shows an embodiment having one temperature sensor for each electrode, there is shown a single power lead 15 for each electrode 32 to provide power to each electrode for ablation purposes and two temperature leads 23 for each temperature sensor 40 to establish the thermocouple effect.

In another approach, the drive wire may comprise one of the thermocouple wires or may comprise a common wire for a plurality of thermocouples mounted on the same electrode. The inventor hereby incorporates by reference U.S. Pat. Nos. 6,045,550 and 6,049,737.

Figures 1, 2:
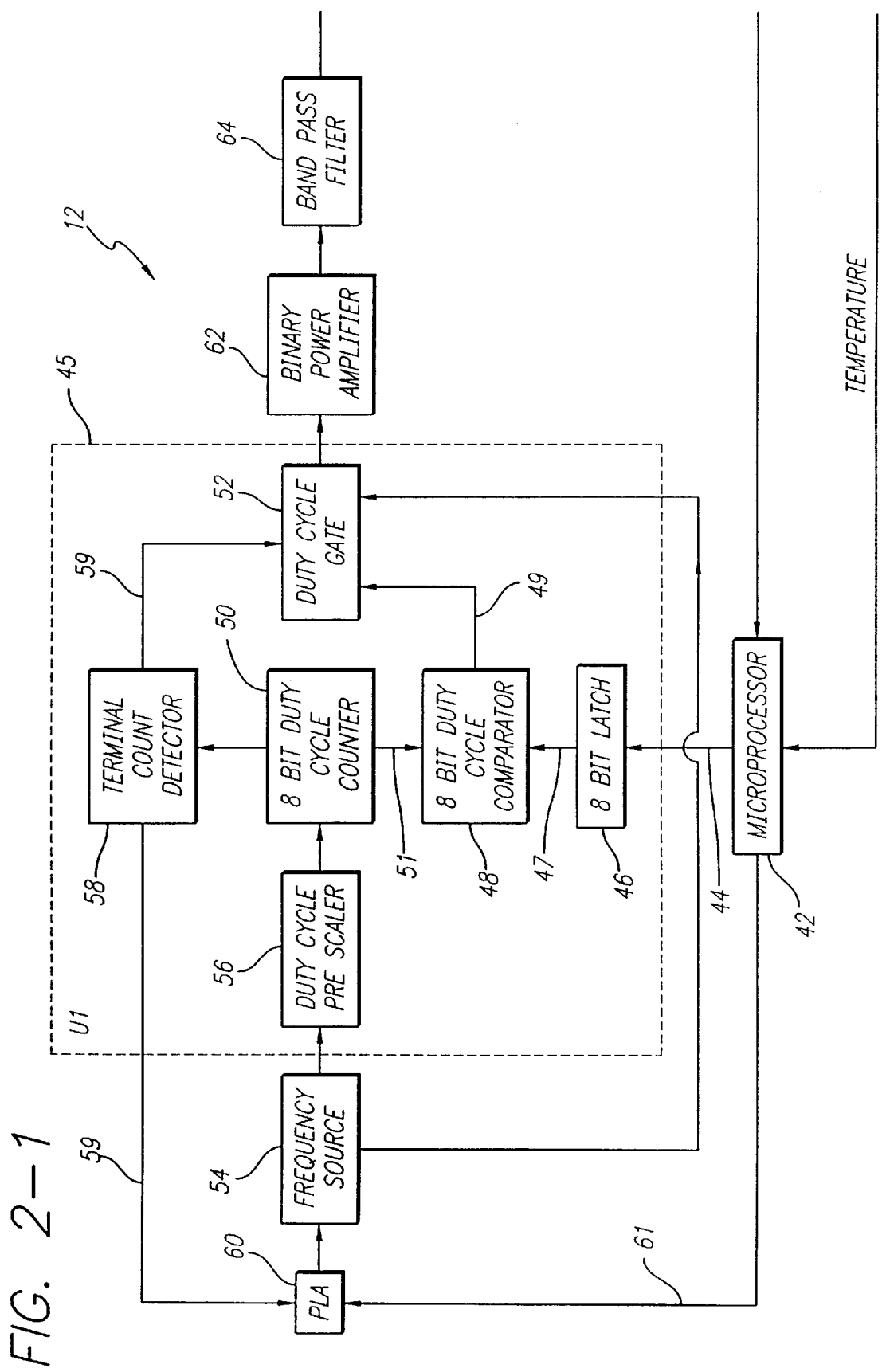
Figure 2:
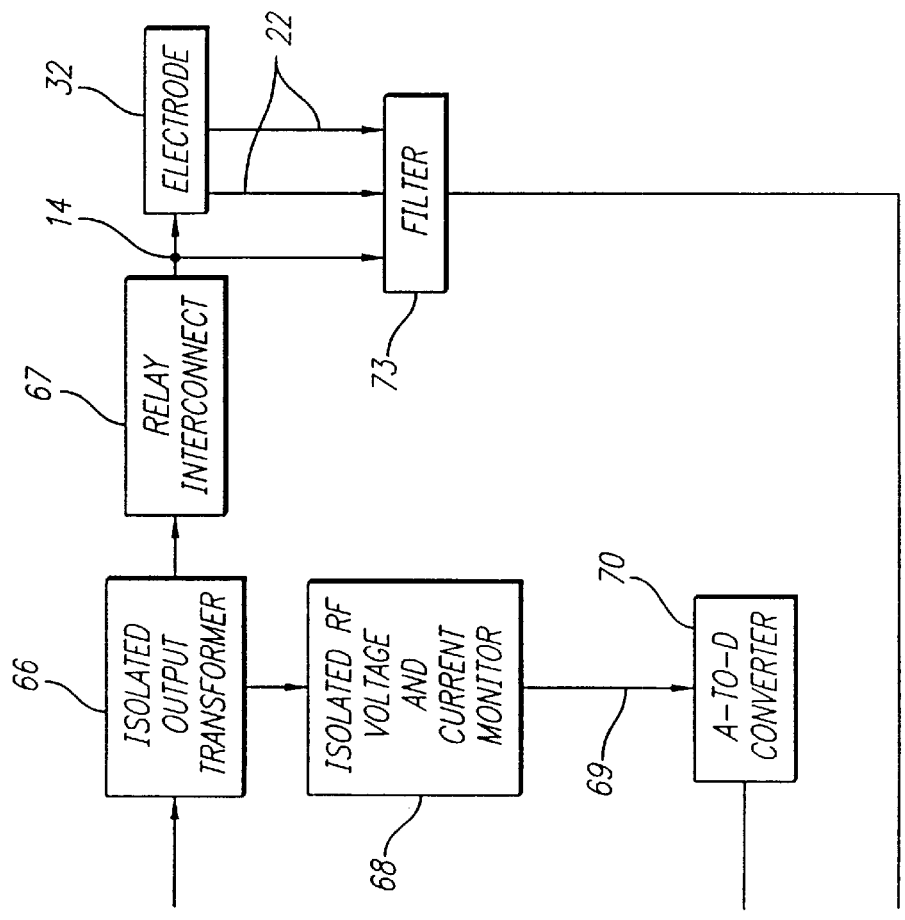

Turning now to FIGS. 2-1 and 2-2, a block diagram of an ablation apparatus 10 and method in accordance with aspects of the invention is presented. In FIGS. 2-1 and 2-2, a single channel of the power control system 12 is depicted. This channel controls the application of power to a single electrode 32. As will be discussed in relation to other figures, a channel may control a plurality or group of electrodes. In FIG. 2-1, a microprocessor 42, which is part of the controller 20 (FIG. 1), provides a duty cycle control signal 44 to a duty cycle generator ("DCG") 45. In this case, the duty cycle generator 45 receives the control signal 44 by an 8-bit latch 46. The latch 46 provides an 8-bit signal 47 to a duty cycle comparator 48. The comparator 48 compares the 8-bit signal 47 to a count from an 8-bit duty cycle counter 50 and if the count is the same, provides a duty cycle off signal 49 to the duty cycle gate 52. The gate 52 is connected to a frequency source ("FS") 54, such as an oscillator that produces 500 kHz. When the gate 52 receives the duty cycle off signal 49 from the comparator 48, it stops its output of the frequency source signal through the gate and no output exists.

At a frequency of 500 kHz, an 8-bit control has a period or time frame of 0.5 msec. At a fifty-percent duty cycle, the electrode is in the off period only 0.25 msec. To allow for greater cooling of the electrode, the period or time frame 78 (FIG. 6) is lengthened by use of a prescalar 56 interposed between the frequency source 54 and the counter 50. In one embodiment, the prescalar 56 lengthens the period to 4 msec thus allowing for a 2 msec off period during a fifty-percent duty cycle. This results in a sufficient cooling time for the very thin band electrodes discussed above. Other lengths of the period may be used depending on the circumstances. It has been found that a ten percent duty cycle is particularly effective in ablating heart tissue. The combination of the application of high peak power, a ten percent duty cycle, the use of high thermal conductivity material in the band electrodes, and fluids flowing past the band electrodes which have a cooling effect on the electrodes result in a much more effective application of power to the tissue. Ablation occurs much more rapidly.

A terminal count detector 58 detects the last count of the period and sends a terminal count signal 59 to the gate 52 which resets the gate for continued output of the frequency source signal. This then begins the on period of the duty cycle and the counter 50 begins its count again. In one preferred embodiment, the duty cycle is set at fifty percent and the 8-bit latch is accordingly set to 128. In another embodiment, the duty cycle is set at ten percent.

A programmable logic array ("PLA") 60 receives phase control signals 61 from the microprocessor 42 and controls the phase of the frequency source 54 accordingly. In one embodiment, the PLA 60 receives the terminal count signal 59 from the terminal count detector 58 and only permits phase changes after receiving that terminal count signal.

The output signal from the gate 52 during the on period of the duty cycle is provided to a binary power amplifier ("BPA") 62 that increases the signal to a higher level, in this case, 24 volts. The amplified signals are then filtered with a band pass filter ("BPF") 64 to convert the somewhat square wave to a sine wave. The band pass filter 64 in one embodiment is centered at 500 kHz. The filtered signal is then provided to an isolated output transformer ("IOT") 66 that amplifies the signal to a much higher level, for example 350 volts peak-to-peak. This signal is then sent to a relay interconnect ("RI") 67 before it is provided as a power output signal OUTn 14 to an electrode 32 at the biological site to cause ablation.

The power output signal 14 from the isolated output transformer 66 is monitored in one embodiment to determine the impedance at the electrode 32. In the embodiment shown in (FIGS. 2-1 and 2-2), a voltage and current monitor ("VCM") 68 is used. The monitor signal 69 is converted to digital form by an A-to-D converter ("ACD") 70 and provided to the microprocessor 42. As previously mentioned, some or all of the electrodes 32 may include a temperature sensor 40 (FIG. 1) that provides temperature signals 22 (FIG. 2-2) which are used to determine the temperature at the electrode 32. In one embodiment of the invention, the power 14, in conjunction with the temperature signals 22, are used to determine the temperature at the electrode 32. Both the temperature signals 22 and the power 14 pass through a temperature filter ("FL") 73 before being sent to the microprocessor 42. In the alternative, the temperature filter ("FL") 73 is contained in a printed circuit board separate from the controller 20 and contains its own processor. In either case, the filter 73 filters out any RF noise present in the power 14 so that the signal may be used for temperature monitoring purposes. In another embodiment, the microprocessor monitors the power 14 and temperature signals 22 only during the off periods of the power 14 duty cycle. Accordingly, negligible RF noise is present in the power line and filtration is not necessary. In either embodiment, the microprocessor 42 may alter the duty cycle of the power 14 in response to either or both of the impedance or temperature signals.

In a manual arrangement, the temperature sensed and/or the determined impedance may be displayed to an operator. The operator in response may then manually control the duty cycle or other power parameters such as by rotating a knob mounted on a front panel of an instrument. In the case of a multiple channel instrument and catheter, as discussed below, multiple knobs may be provided in this manual arrangement for control over each channel.

Figure 3:
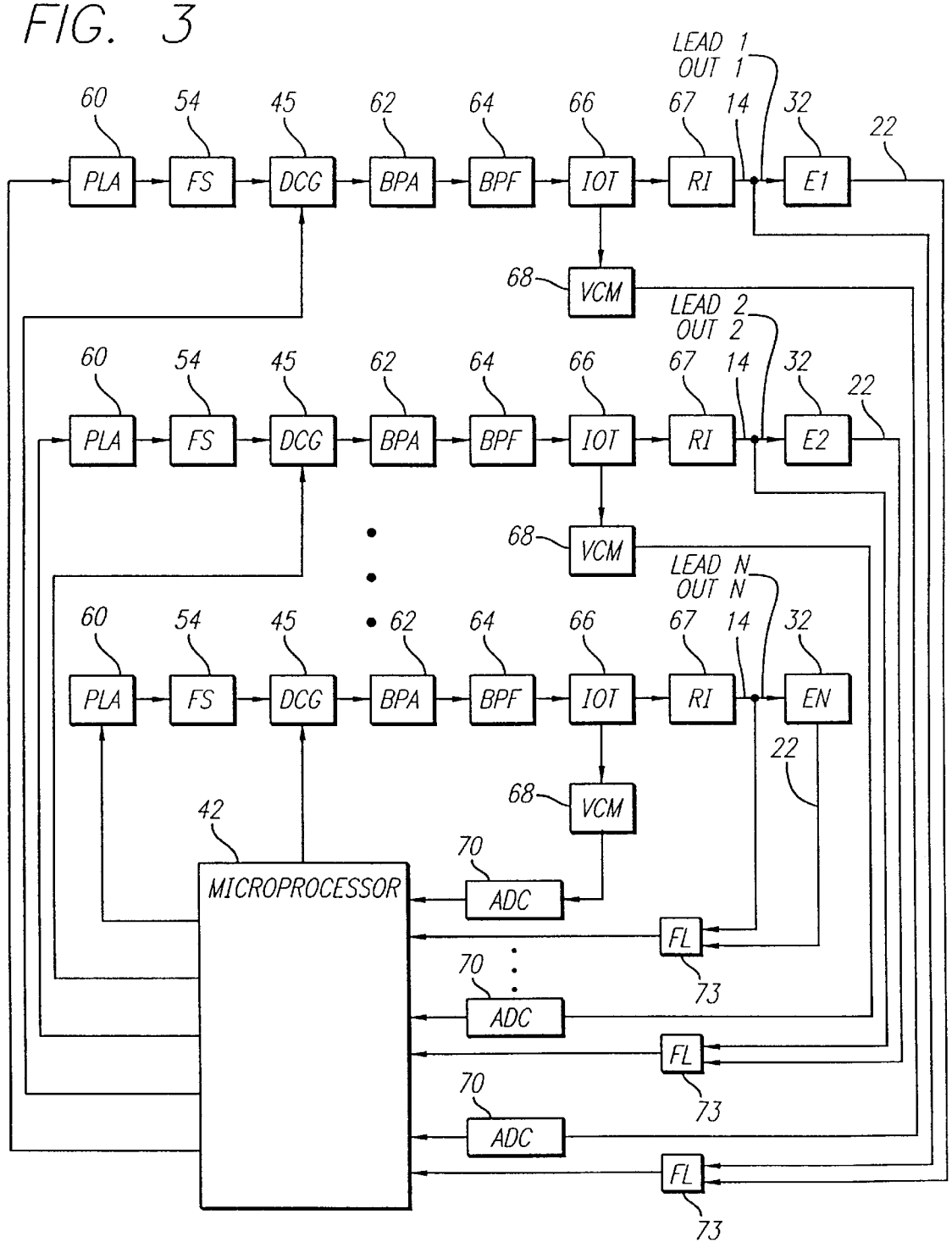
FIG. 3 is a diagram of a multi-channel ablation apparatus in accordance with aspects of the invention wherein a single microprocessor controls the phase angle and duty cycle of each channel individually.

Referring now to FIG. 3, a multiple channel ablation apparatus is shown. Although only three complete channels are shown, the apparatus comprises many more as indicated by the successive dots. Those channels are not shown in FIG. 3 to preserve clarity of illustration. By providing different voltage levels between two electrodes 32 in an array, current flows between those electrodes in a bipolar electrode approach. By setting the backplate 24 (FIG. 1) at a voltage level different from at least one of those electrodes 32, current flows between that electrode and the backplate. By controlling the voltage levels among the three (two electrodes and backplate), the current flow through the biological site 26 can be more precisely controlled. One technique for setting different voltage levels between the electrodes 32 is to maintain a phase difference between them in an AC approach. By setting the backplate 24 at the reference level, current flows between the electrodes 32 and the backplate.

The single microprocessor 42, which again is part of the controller 20 (FIG. 1), controls the duty cycle and the phase of each channel individually in this embodiment. Each channel shown comprises the same elements and each channel produces its own power output signal 14 (OUT1, OUT2, through OUTn where "n" is the total number of channels) on respective electrode leads (LEAD 1, LEAD 2, through LEAD n where "n" is the total number of leads) to the electrodes 32. This multi-channel approach permits more individual control over each electrode. For example, the duty cycle of the power applied to each electrode can be individually controlled. One electrode may have a ten percent duty cycle while another has a thirty percent duty cycle.

Figure 4:
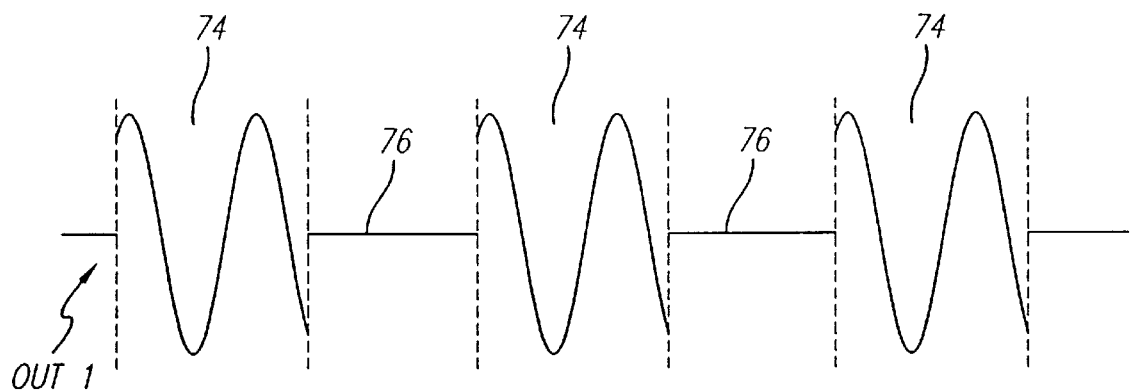
FIG. 4 depicts a first power waveform having a first phase angle and alternating instances of peak power and very low power.
Figure 5:
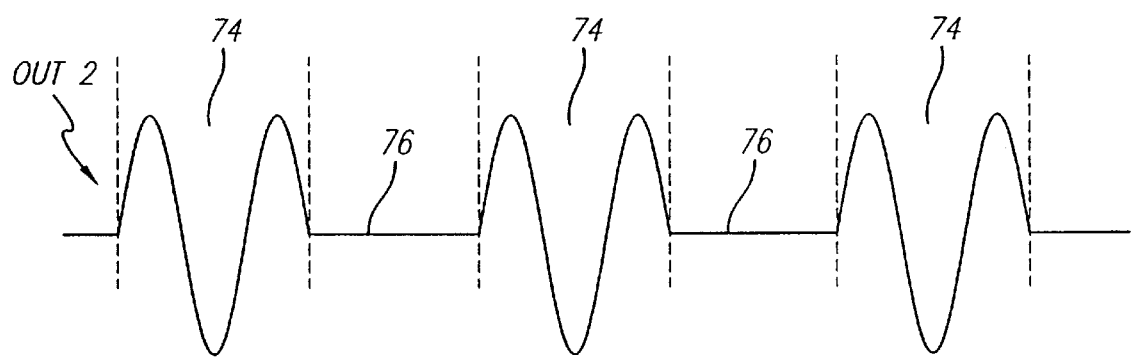
FIG. 5 depicts a second power waveform having a second phase angle different from the first phase angle and alternating instances of peak power and very low power.
Figure 6:
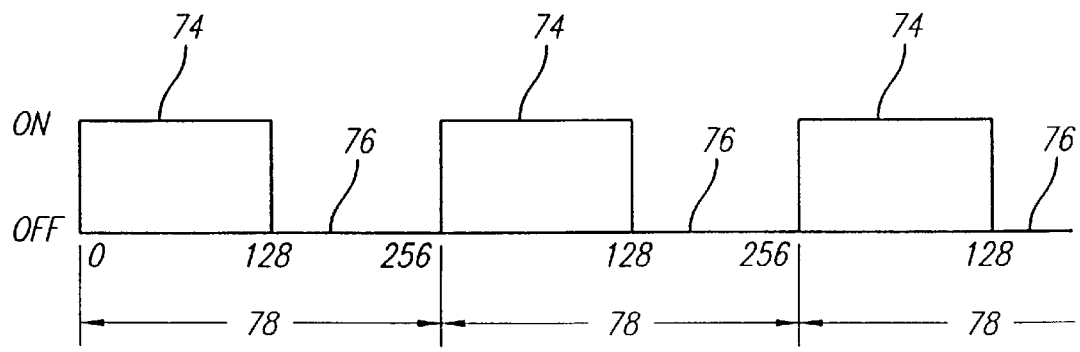
FIG. 6 presents a time frame (TF) diagram showing a fifty-percent duty cycle.

Referring now to the first and second output signals OUT1 and OUT2 of FIG. 3, the signals, as shown in FIGS. 4, 5, and 6, have alternating instances of peak power i.e., "on" periods 74, and very low power 76, i.e., "off" periods. Typically, the output power 14 is a 500 kHz sine wave. In FIGS. 4 and 5, the number of cycles of the sine wave contained within one on period 74 has been substantially reduced in the drawing to emphasize the phase difference between the first and second output signals OUT1, OUT2. Preferably, the voltage of each power signal 14 during an off period 76 is substantially zero and during an on period 74 is approximately 350 volts peak-to-peak.

The power OUT1 and OUT2 also have a variable duty cycle for controlling the length of the on period 74 and the off-period 76 within a time frame 78 (see FIG. 6). The duty cycle is the ratio of the length of the on period 74 to the length of the entire time frame 78. The effective power is the peak power times the duty cycle. Thus, a signal having a peak power of 100 watts and a 50% duty cycle has an effective power of 50 watts.

Figure 7B:
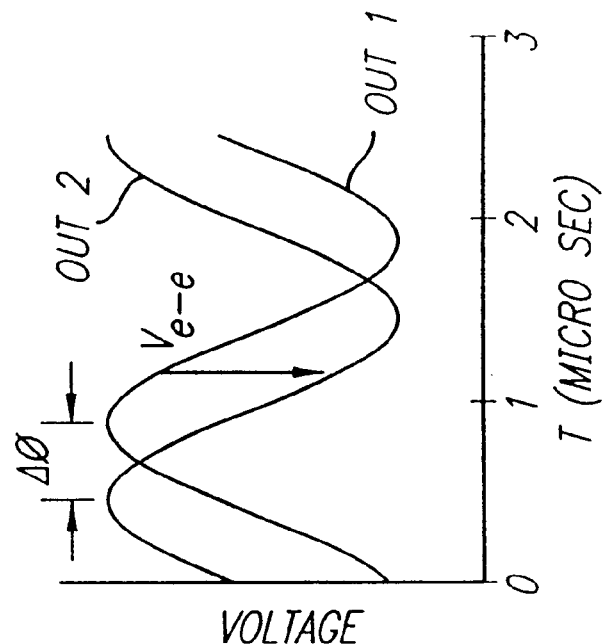
FIG. 7B depicts the phase relationship and voltage potential between the first and second power waveforms having second and first phase angles respectively, as a function of time.
Figure 7A:
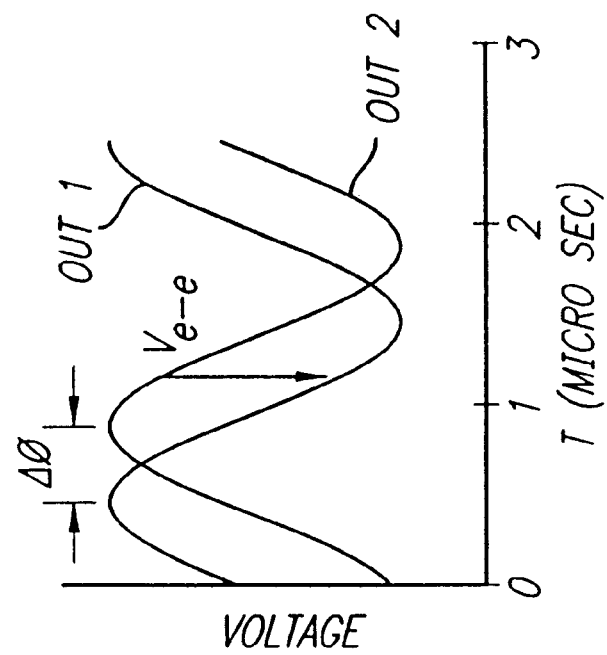
FIG. 7A depicts the phase relationship and voltage potential between the first and second power waveforms having first and second phase angles respectively, as a function of time.

As shown in FIGS. 4, 5, and 6, the two power signals OUT1, OUT2 are phased differently from each other. As discussed above, the phase angle of each power signal is set and controlled by the processor 42 and PLA 60. Each power signal OUT1 and OUT2 has a respective phase angle and those phase angles differ between the two of them. The phase angle difference between the power OUT1 and OUT2 produces a voltage potential between the band electrodes 32 (FIG. 1) that receive the power. This voltage potential, in turn, induces current flow between the band electrodes 32 The phase angle relationship of the power and the voltage potential produced as a function of time is shown in FIGS. 7A and 7B. The potential between electrodes $V_{e-e}$ is defined by:

$$V_{e-e} = 2V\sin\left(\frac{\Delta\Phi}{2}\right)\sin(2\pi ft) \tag{Eq. 1}$$

where:
$\Delta\Phi$=phase angle difference between electrodes
V=voltage amplitude of power
f=frequency in hertz
t=time FIG. 7A shows first and second power OUT1 and OUT2 provided to first and second electrodes respectively having a phase angle difference $\Delta\Phi$ with OUT1 leading OUT2 by 132 degrees. FIG. 7B shows the same power OUT1 and OUT2 but with the phase angles reversed where OUT2 is now leading OUT1 by 132 degrees.

Figure 8C:
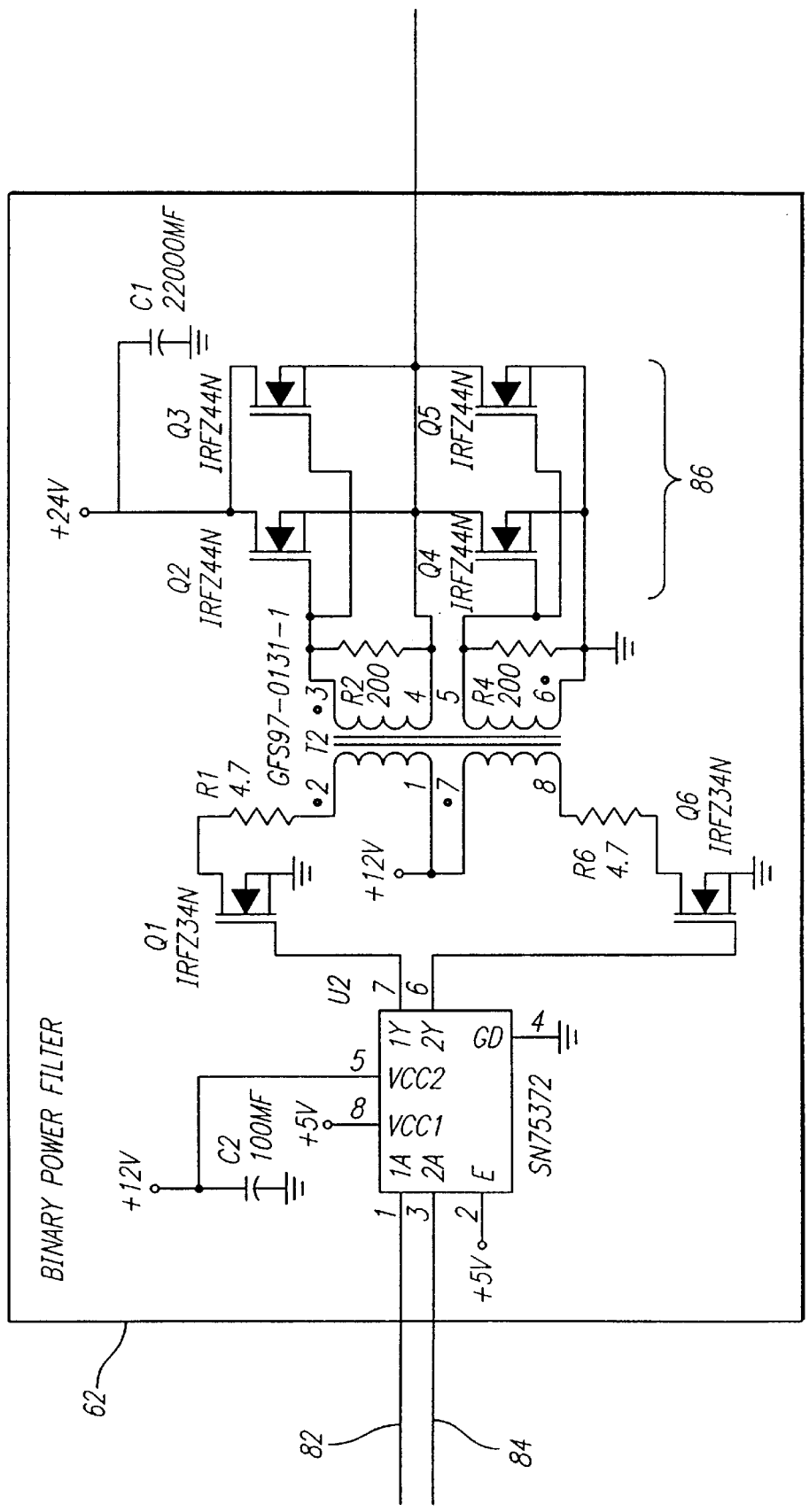
Figure 8D:
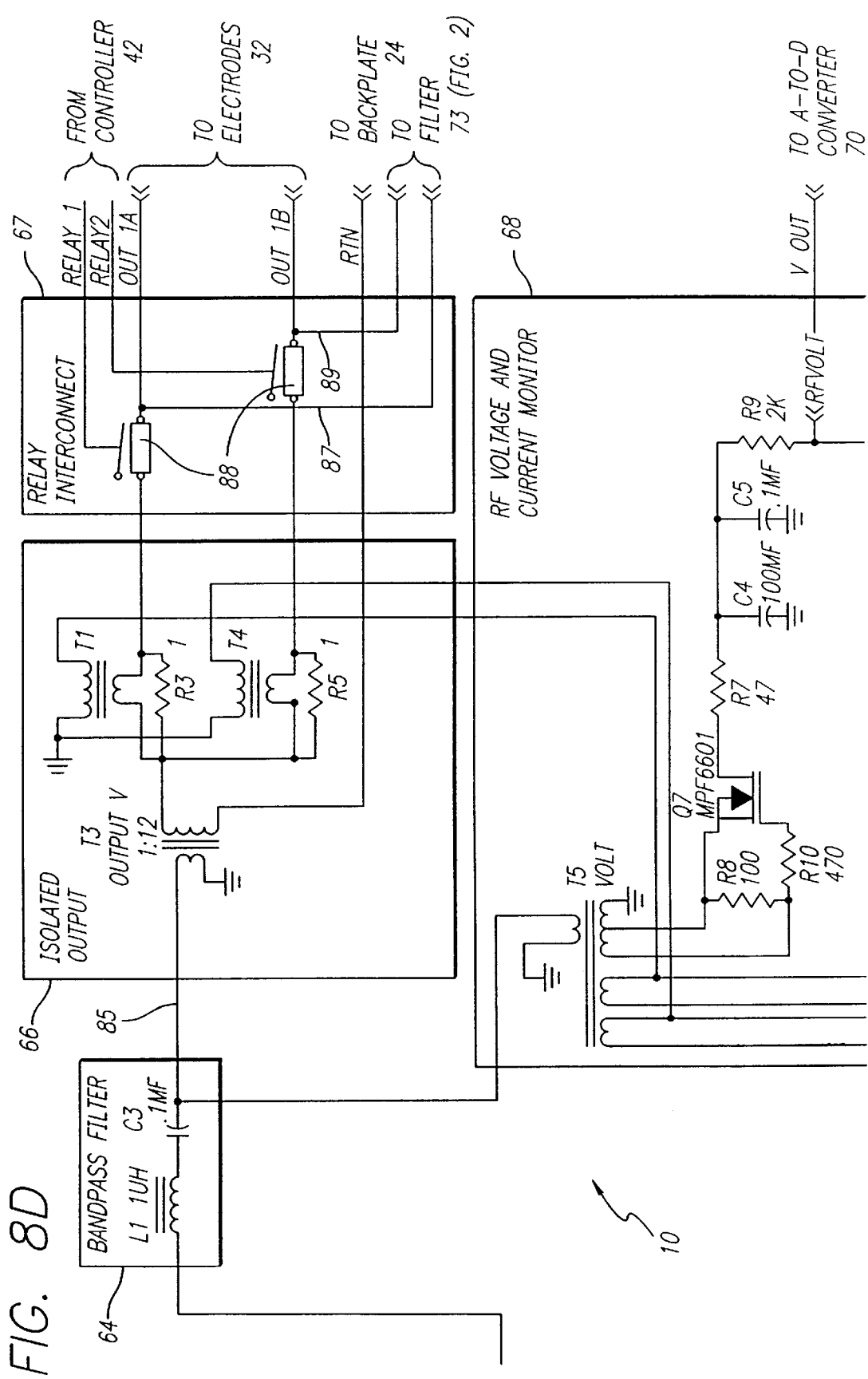
Figure 8E:
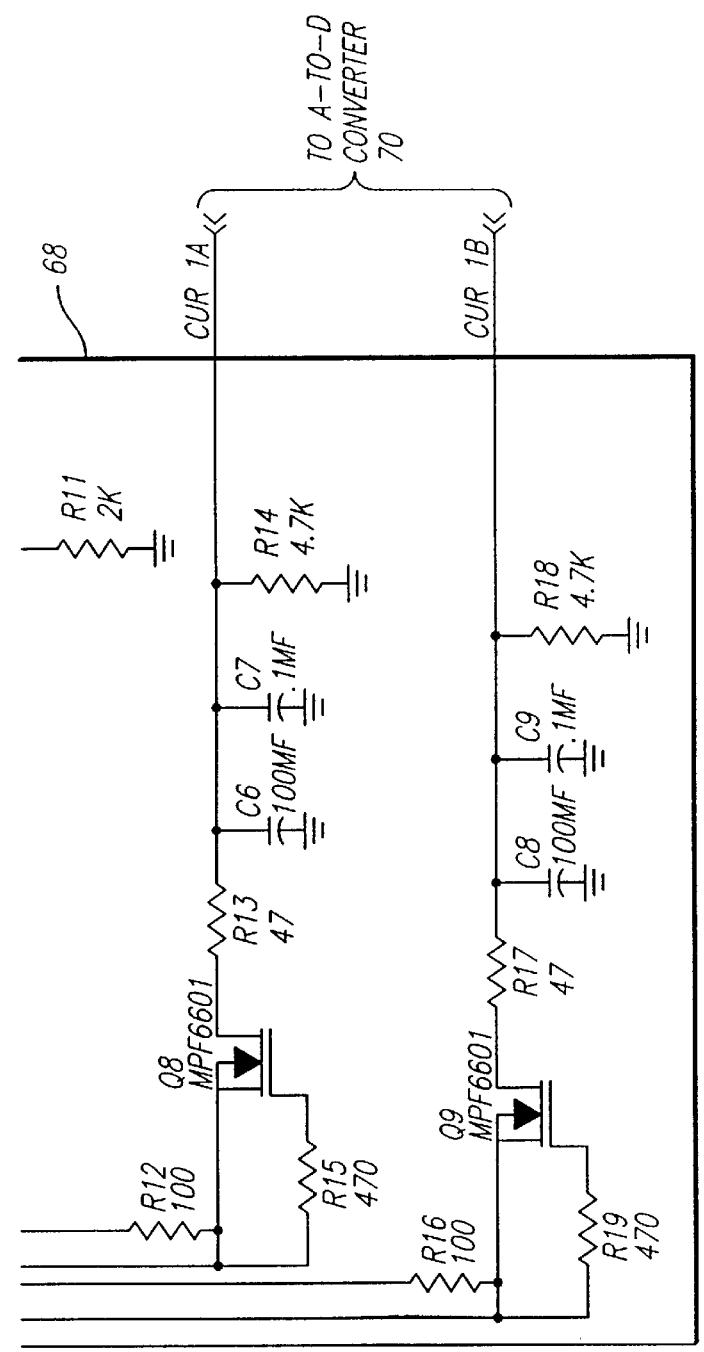
Figure 9A:
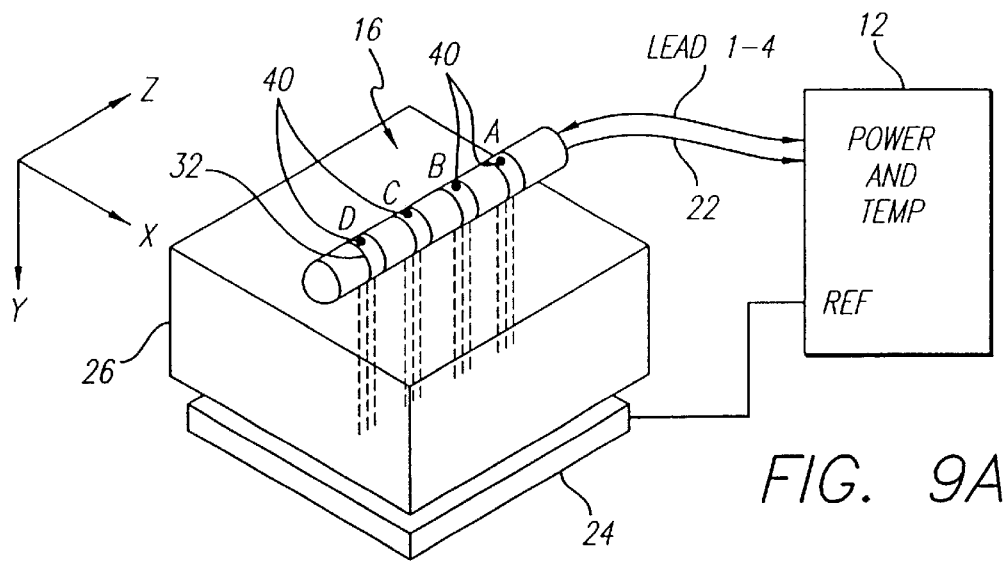
FIG. 9A is a three dimensional representation of an ablation apparatus having a linear array of band electrodes in contact with a biological site with a backplate at the opposite side of the biological site, in which the phase angle difference between adjacent electrodes of the linear array is zero degrees.
Figure 9B:
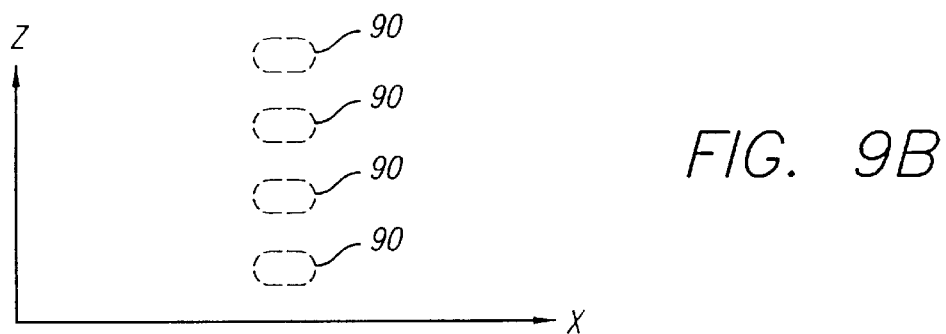
FIGS. 9B through 9D depict, along the x, y, and z axes shown, the depth of the lesions formed by the ablation apparatus of FIG. 9A showing that the apparatus acts as a unipolar device with multiple electrodes and the resulting lesions are discontinuous.
Figure 9C:
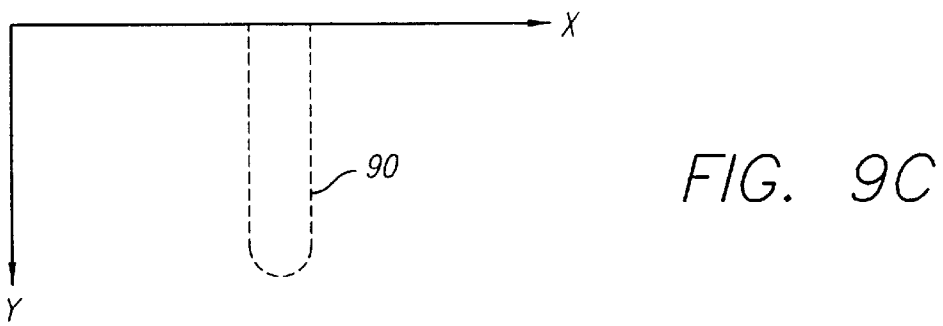
Figure 9D:
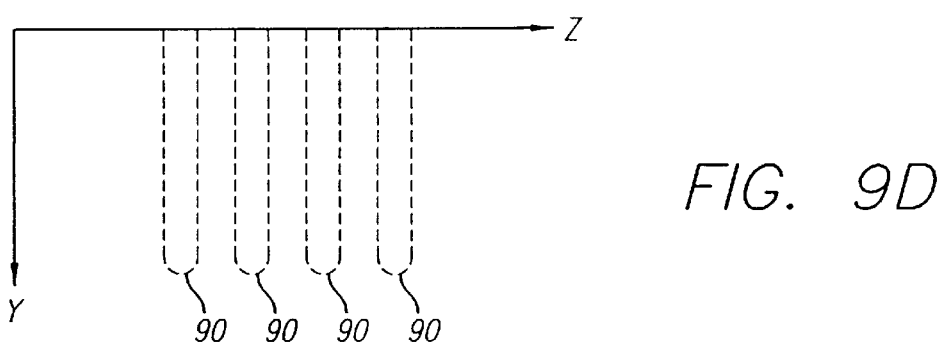

With reference now to FIGS. 8A–8E, schematic diagrams of an embodiment of the ablation apparatus 10 of FIGS. 2-1 and 2-2 are presented in FIGS. 8B through 8E while FIG. 8A shows how FIGS. 8B through 8E should be oriented in relation to each other. The frequency source 54 provides a signal 80, typically at 500 kHz with a phase angle controlled by the microprocessor 42 through the PLA 60, to the duty cycle generator 45. The duty cycle generator 45 modulates the frequency source signal 80 to produce the selected duty cycle in accordance with the duty cycle control signal 44 as previously described. The duty cycle generator 45 outputs two signals 82 and 84 to the binary power amplifier 62. A dual MOSFET driver U2 receives the signals, converts their 5 V level to a 12 V level, and sends each to a transformer T2 which transforms the signals into 24 V peak-to-peak power.

The 24 V power is then sent to a multi-state driver 86 which includes a configuration of FETs Q2, Q3, Q4, and Q5. During a conducting state of the driver 86, which is typically the on period 74 of the power, these FETs Q2 through Q5 conduct and forward the power to a bandpass filter 64 comprising a series LC network. During a high-impedance state of the driver 86, which is typically during the off period 76 of the power, the FETs Q2 through Q5 are nonconducting and no power is sent to the bandpass filter 64. Instead the FETs Q2 through Q5 present a high impedance load to any signals received through the electrode 32. Typically the load impedance on the FETs Q2 through Q5 presented by the circuit following the FETs, the electrode, and the tissue is approximately 150 Ω but transformed through the output transformer T3, it presents a load impedance to the FETs Q2–Q5 of approximately 0.5 to 1 Ω. In the off state, the FETs present an impedance of approximately 250 Ω which is large in comparison to the transformed load impedance of approximately 0.5 to 1 Ω. Therefore, very little power flows when the FETs are in the off state.

The bandpass filter 64 operates to shape the output signal provided by the binary amplifier 62 from a square wave to a sinusoidal wave. The filtered signal 85 then passes to the isolated output section 66 where it is step-up transformed to 350 volt peak-to-peak sinusoidal power at T3. The power is then split into two identical power signals OUT1A, OUT1B and provided to two or more respective band electrodes 32 on the output lines LEAD1A, LEAD1B.

The isolated output section 66 also includes relays 88 that may be individually opened to remove the power signals OUT1A, OUT1B from the electrode leads LEAD 1A, LEAD 1B when an alert condition is detected, such as high temperature or high impedance at the respective electrode 32. As previously mentioned these conditions are determined by the microprocessor 42 which receives signals indicative of the temperature and impedance at each of the band electrodes 32.

The power from the isolated output section 66 is monitored and representative signals are supplied to an RF voltage and current monitor 68 where in this case, the voltage and current of each output signal are measured to determine the impedance of the particular channel. The measured signals are sent to an A-to-D converter 70 (FIG. 2-2) before being sent to the microprocessor 42 for impedance monitoring. If the impedance is above a threshold level indicative of blood clotting or boiling, the microprocessor 42 sends a signal to the duty cycle generator 45 to reduce or discontinue the duty cycle of the power OUT1A, OUT1B and thus lower the effective power delivered to the band electrodes 32.

Similarly, the temperature at the electrodes 32 is determined by monitoring the power 14 and temperature signals 22 and measuring the voltage difference between the signals. As previously mentioned, in one embodiment of the invention, these signals pass through a filter 73 (FIG. 2-2) before being sent to the microprocessor 42. The voltage value is converted to a temperature and if the temperature is above a threshold level the duty cycle of the power 14 is reduced. In the case where a single lead is used to provide a signal which is used to determine the temperature as well as provide power to the electrode 32, the signal from the lead is received on temperature leads 87, 89 connected at the output side of the relays 88.

As shown in FIG. 3, the duty cycle of each electrode 32 may be individually controlled by the microprocessor 42. As previously mentioned, based on the temperature at an electrode 32 and the current and voltage of the output signal provided to an electrode, the duty cycle of the output signal may be adjusted. For example, one electrode 32 may have a temperature requiring a duty cycle of ten percent, while another electrode may have a temperature which allows for a fifty percent duty cycle. In an embodiment in which every other electrode 32 has a temperature sensor 40, the electrodes are grouped in pairs with each electrode in the pair having the same duty cycle.

In operation, as depicted in FIGS. 9a through 11d, the electrode device 16 and the backplate 24 are positioned proximal the biological site 26 undergoing ablation such that the biological site is interposed between the electrode device and the backplate. The band electrodes 32 (only one of which is indicated by a numeral 32 for clarity of illustration) of the electrode device 16 each receives power OUT1, OUT2, OUT3, OUT4 having a phase angle on LEAD 1 through LEAD 4. In one embodiment, every other electrode 32 receives the same phase angle. Therefore, the phase angle of electrode A equals the phase angle of electrode C and the phase angle of electrode B equals the phase angle of electrode D. The advantages of this arrangement are described below. In a preferred embodiment, the electrodes 32 are formed into a linear array as shown. In addition, a thermocouple temperature sensor 40 is located at each of the electrodes A, B, C, and D and uses the electrode power lead LEADS 1 through 4 as one of the sensor leads. The sensors 40 provide temperature sensor signals 22 for receipt by the power control system 12.

In another embodiment, alternate electrodes 32 may be grouped together and each may receive the same power having the same phase angle and duty cycle. Another group or groups of electrodes 32 may be interspaced with the first group such that the electrodes of one group alternate with the electrodes of the other group or groups. Each electrode 32 in a particular group of electrodes has the same phase angle and duty cycle. For example, electrodes A and C may be connected to the same power while interspaced electrodes B and D may be connected to a different power output signal.

The use of individual power signals also provides the ability to disable any combination of electrodes 32 and thereby effectively change the length of the electrode device 16. For example, in one configuration of the present invention an electrode device 16 with twelve electrodes 32 receives twelve power signals from a twelve channel power control system 12. The electrodes 32 are 3 mm in length and are 4 mm apart. Accordingly, by disabling various electrodes, a virtual electrode of any length from 3 mm to 8 cm may be produced by the electrode device 16. In either arrangement the backplate 24 is maintained at the reference voltage level in regard to the voltage level of the power OUT1 through OUTn.

As previously described, by varying the phase angles between the power OUT1, OUT2 supplied to each electrode 32, a phase angle difference is established between adjacent band electrodes. This phase angle difference may be adjusted to control the voltage potential between adjacent band electrodes 32 and thus to control the flow of current through the biological site 26. The flow of current $I_{ee}$ between adjacent band electrodes 32 is defined by:

$$I_{e-e} = \frac{2V\sin\left(\frac{\Delta\Phi}{2}\right)\sin(2\pi ft)}{Z_{e-e}} \quad \text{(Eq. 2)}$$

where:

$\Delta\Phi$=phase angle difference between electrodes

V=voltage amplitude of power $Z_{e-e}$=impedance between electrodes f=frequency in hertz t=time In addition to the current flow between the band electrodes 32 there is current flow between the band electrodes and the backplate 24. When the backplate 24 is set at the reference level, this current flow $I_{e-b}$ is defined by:

where:

$\Delta\Phi$=phase angle difference between electrodes

V=voltage amplitude of power $Z_{e-b}$=impedance between electrode and backplate f=frequency in hertz t=time Assuming $Z_{e-b}$ and $Z_{e-e}$ are equal, the ratio of the current flowing between the band electrodes 32 $I_{e-e}$ to the current flowing between the band electrodes 32 and the backplate 24 $I_{e-b}$ is defined by:

where:

$\Delta\Phi$=phase angle difference between electrodes

FIGS. 9 through 11 illustrate various current flow patterns within a biological site. The depths and widths of the lesions depicted in FIGS. 9A through 11D are not necessarily to scale or in scalar proportion to each other but are provided for clarity in discerning the differences between the various power application techniques. When the phase difference between adjacent electrodes 32 is zero degrees, no current flows between the electrodes in accordance with Eq. 2 above, and the apparatus operates in a unipolar fashion with the current flowing to the backplate 24 as shown in FIGS. 9A through 9D. Substantially all current flows from the band electrodes 32 to the backplate 24 forming a series of relatively deep, acute lesions 90 along the length of the electrode device 16. As seen in the top view of FIG. 9B and the side view of FIG. 9D, the lesions are discrete. The lesions 90 are discontinuous in regard to each other.

Figure 10A:
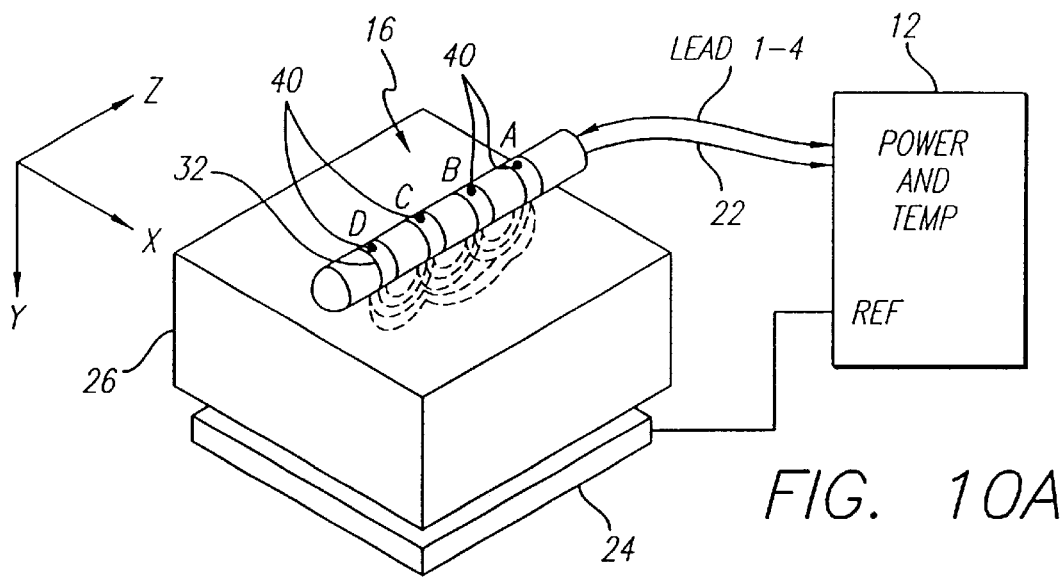
FIG. 10A is a three dimensional representation of an ablation apparatus having a linear array of band electrodes in contact with a biological site with a backplate at the opposite side of the biological site, in which the phase angle difference between adjacent electrodes is 180 degrees.
Figure 10B:
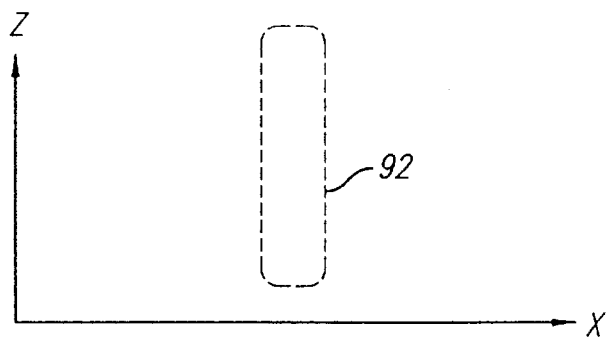
FIGS. 10B through 10D depict, along the x, y, and z axes shown, the continuity and depth of a lesion formed by the ablation apparatus of FIG. 10A showing that the apparatus acts as a bipolar device with no significant amount of current flowing to the backplate.
Figure 10C:
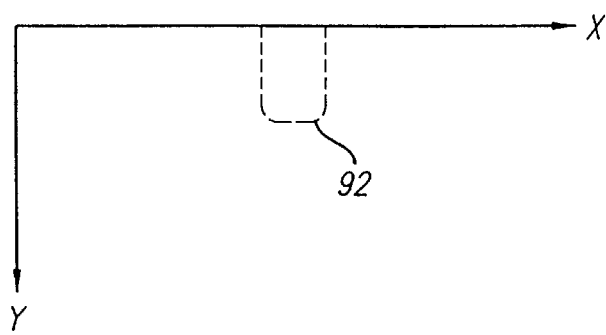
Figure 10D:
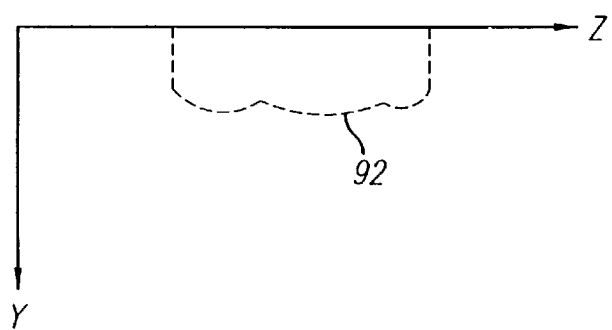

When the phase difference between adjacent electrodes 32 is 180 degrees the apparatus operates in both a unipolar and bipolar fashion and the current flow pattern is as shown in FIG. 10A. With this phase difference, approximately twice as much current flows between adjacent band electrodes 32 than flows from the band electrodes to the backplate 24. The resulting lesion 92 is shallow but is continuous along the length of the electrode device 16. The continuity and shallow depth of the lesion 92 are illustrated in FIGS. 10B through 10D. Nevertheless, the lesion depth is still greater than that created by prior bipolar ablation methods alone.

Figure 11A:
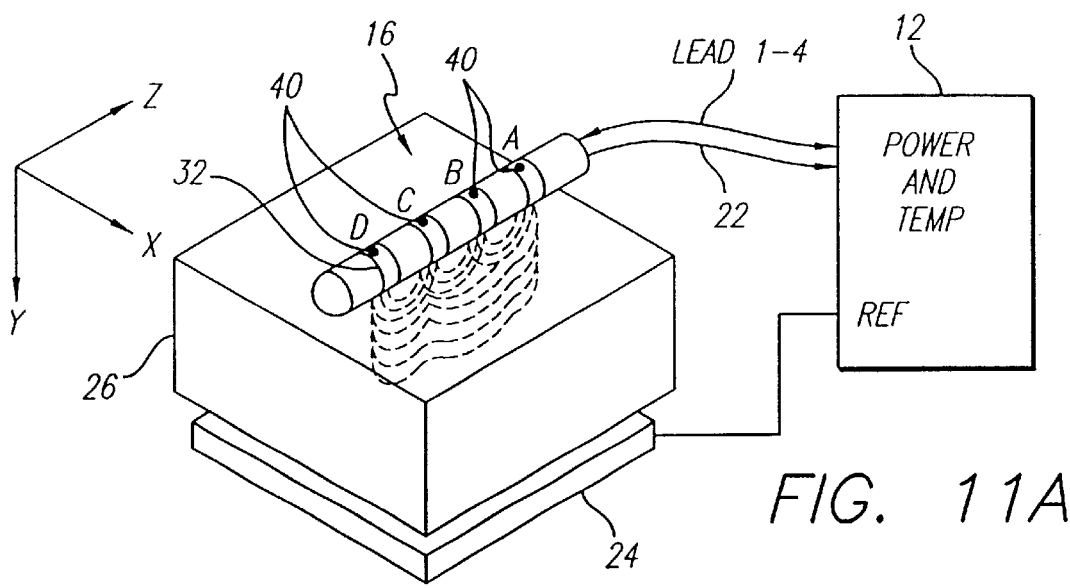
FIG. 11A is a three dimensional representation of an ablation apparatus having a linear array of band electrodes in contact with a biological site with a backplate at the opposite side of the biological site, in which the phase difference between adjacent electrodes is approximately 90 degrees.
Figure 11B:
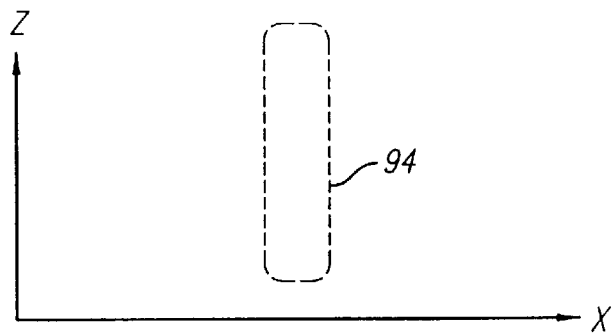
FIGS. 11B through 11D depict, along the x, y, and z axes shown, the continuity and depth of a lesion formed by the ablation apparatus of FIG. 11A showing the greater depth of lesion resulting from the phase angle difference.
Figure 11C:
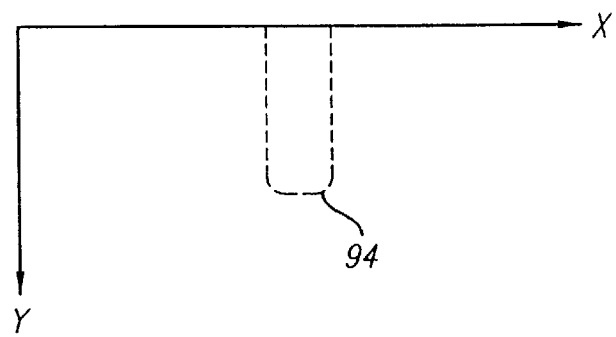
Figure 11D:
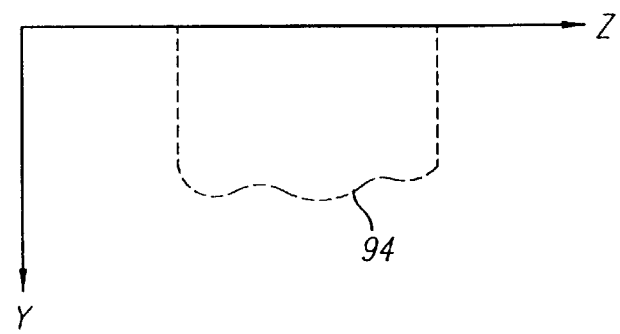

When the phase difference between adjacent electrodes 32 is set within the range of a value greater than zero to less than 180 degrees, the current flow varies from a deep, discontinuous unipolar pattern to a more continuous, shallow bipolar pattern. For example, when the phase difference between adjacent electrodes 32 is around 90 degrees, the current flows as shown in FIG. 11A. With this phase difference, current flows between adjacent band electrodes 32 as well as between the band electrodes and the backplate 24. Accordingly, a lesion which is both deep and continuous along the length of the electrode device 16 is produced. The continuity and depth of the lesion 94 is illustrated in FIGS. 11B through 11D. In one embodiment of FIG. 11A, adjacent electrodes alternated in phase but were provided with power in groups. Electrodes A and C were provided with power at a first phase angle and electrodes B and D were provided with power at a second phase angle, different from the first.

Thus, in accordance with the present invention the phase angle of the power may be adjusted in order to produce a lesion having different depth and continuity characteristics. In selecting the phase angle difference necessary to produce a continuous lesion having the greatest possible depth, other elements of the electrode device 16 are considered. For example, the width of the band electrodes 32 and the spacing between the electrodes are factors in selecting an optimum phase angle. In a preferred embodiment of the present invention, as pointed out above, the width of the band electrodes is 3 mm, the spacing between the electrodes is 4 mm and the electrodes receive power which establish a phase difference of 132 degrees between adjacent electrodes. With this configuration a long continuous lesion having a length of between approximately 3 mm and 8 cm and a depth of 5 mm or greater was produced depending on the number of electrodes energized, the duty cycle employed, and the duration of power application.

In another embodiment of the invention, energy is applied to the biological tissue 26 during the on period of the duty cycle in an alternating unipolar-bipolar manner. During the unipolar mode segment a voltage potential is established between the electrodes 32 and the backplate 24. Thus current flows through the tissue 26 between the electrodes 32 and the backplate 24.

During the bipolar mode segment a voltage potential is established between at least two of the electrodes 32 rather than between the electrodes and the backplate 24. Thus current flows through the tissue 26 between the electrodes 32. While operating in this mode the voltage difference between the electrodes 32 may be established by providing power with different phase angles to the electrodes as previously mentioned. Alternatively, some of the electrodes 32 may be connected to a reference potential while others are maintained at a different voltage level.

By adjusting the duration of the unipolar and bipolar mode segments within the on period of the duty cycle, the continuity and depth of the lesion produced may be controlled. For example, operating in the unipolar mode for one-fourth of the on period and in the bipolar mode for three-fourths of the on period produces a lesion having a continuity and depth similar to the lesion 94 illustrated in FIGS. 11B through 11D.

Referring to FIGS. 8B through and 8E, the following devices are shown:
The transformer denoted by "T3" is a 1:12 turns ratio, single turn primary, step up transformer wound on a TDK core PC50EER23Z.

Figure 12:
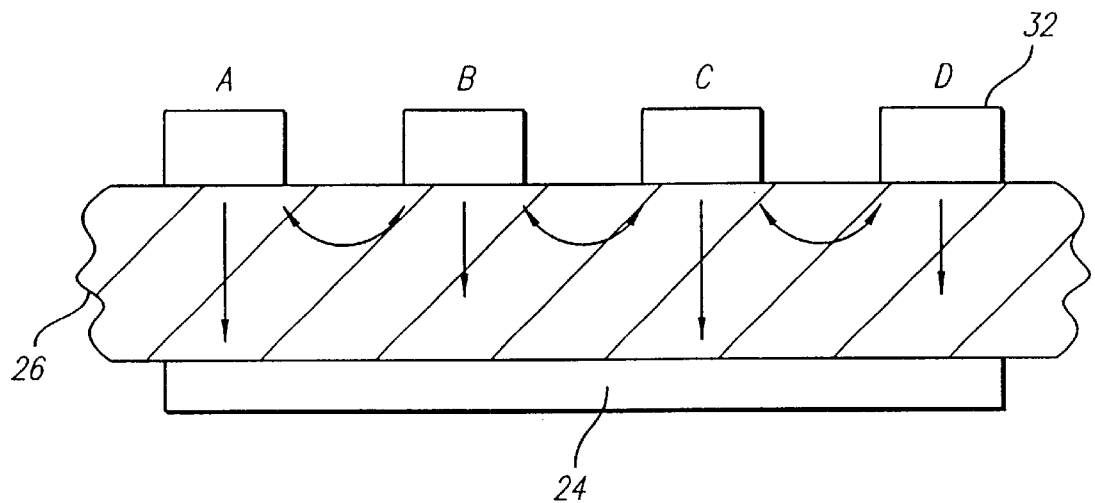
FIG. 12 presents a block diagram of the current flow among electrodes and the backplate through the biological site for adjacent electrodes having different phase angles.

FIG. 12 presents a block diagram of the current flow among electrodes 32 and the backplate 24 through the biological site 26 for adjacent electrodes having different phase angles where the phase angles of the A and C electrodes lead the phase angles of the B and D electrodes. It has been noted that with the approach shown in FIG. 12, the vector sum of the currents flowing through the site 26 is such that more current flows at one or more electrodes than at others. This is shown figuratively with shorter arrows leading to the backplate from the B and D electrodes. Although the ablation volume is greater than in the prior techniques, the ablation volume appears irregular or non-uniform as shown in FIG. 11D. It is desirable to have a more uniform ablation volume, especially as to depth, so that irregular electrical signals do not pass under the ablation volume at a point having less depth and require a repeat of the ablation procedure.

Figure 13:
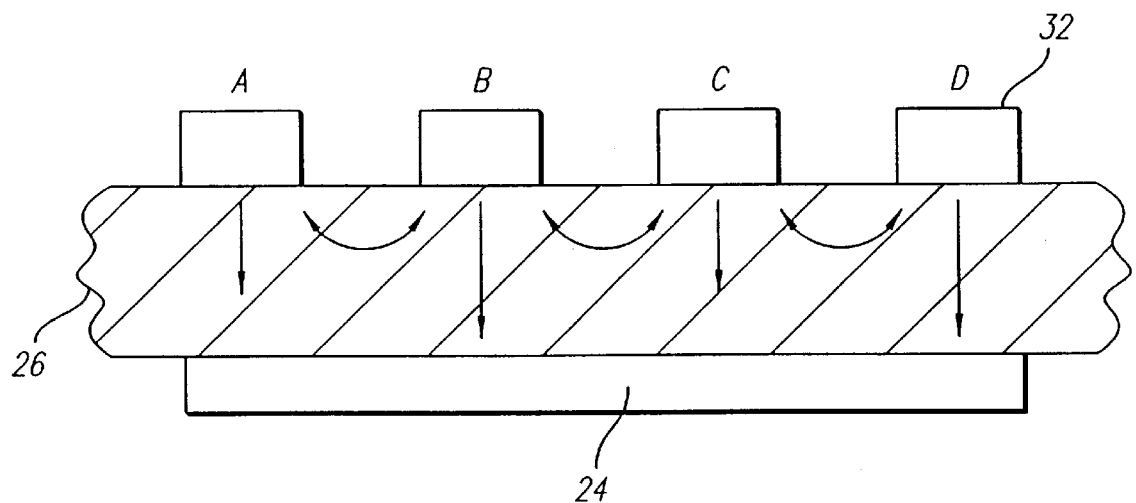
FIG. 13 presents the same block diagram as FIG. 12 with the phase angles between adjacent electrodes reversed.
Figure 14A:
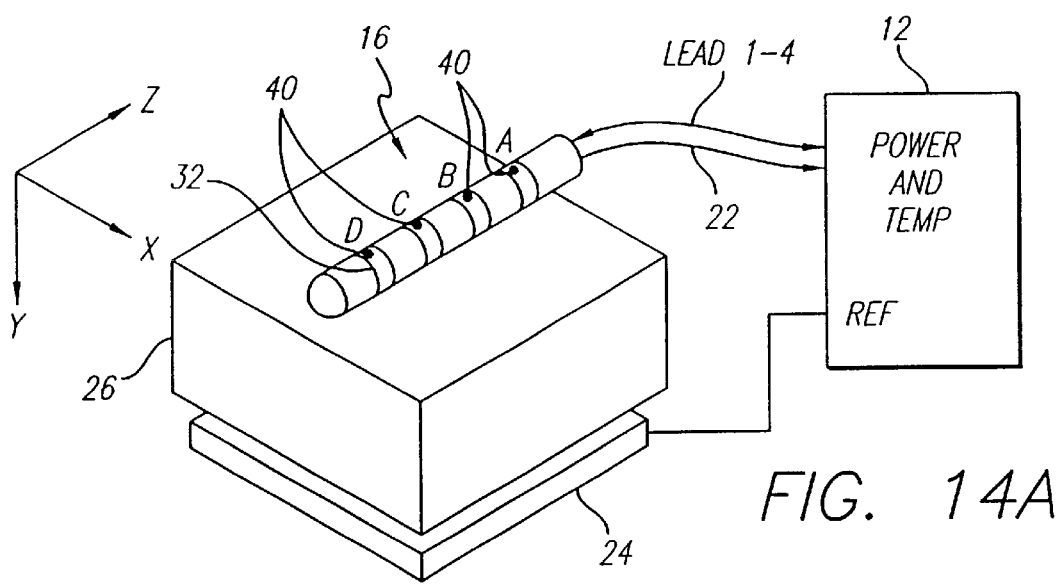
FIGS. 14A through 14D present, along the x, y, and z axes shown, the increased continuity, depth, and uniformity of a lesion formed by the alternating phase apparatus and method shown in previous figures.
Figure 14B:
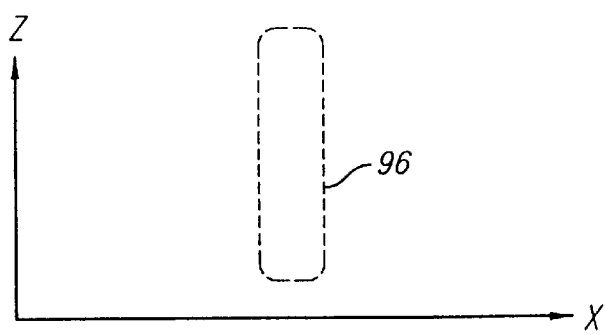
Figure 14C:
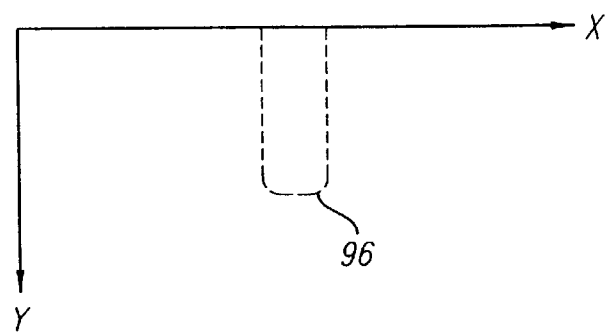
Figure 14D:
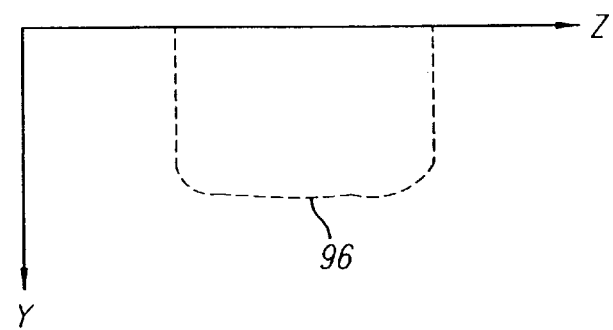

FIG. 13 presents the same block diagram as FIG. 12 with the phase angles between adjacent electrodes reversed. In FIG. 13, the phase angles of the power at the B and D electrodes 32 now lead the phase angles of the power at the A and C electrodes 32. The change in current flow due to this opposite phasing is represented figuratively with shorter arrows now at the A and C electrodes thus balancing the current flow pattern of FIG. 12. It has been found that by alternating the phase angles such as shown in FIGS. 12 and 13, a much more uniform current flow and much more uniform ablation volume result. A cumulative effect of the current flow causes the tissue between all the band electrodes 32 and the backplate 24 to become ablated, depth-wise through the biological site 26, at a substantially even rate and thus a lesion having substantially uniform depth is produced. This is shown in FIGS. 14A through 14D where an ablation volume 96 is shown, which has much greater uniformity in shape. In particular, the ablation lesion 96 has a uniform depth and gives rise to a high level of confidence that the ablation volume created with the ablation apparatus in accordance with the invention will successfully destroy the tissue causing the arrhythmia.

In one embodiment, the phase between the electrodes was alternated as shown in FIGS. 12 and 13 only during the off period of the duty cycle. That is, and with reference to FIG. 6, during the entire on period 74 of the duty cycle of one time frame 78, the phase angles of the power at the A and C electrodes 32 led the phase angles of the power at the B and D electrodes 32 by 132 degrees. During the following off period 76 of the same time frame 78, the phase angles of the power to be supplied was changed to be opposite those phase angles used during the on period 74, in preparation for the next on period. Then at the next on period 74, the phase angles of the power provided to electrodes B and D led the phase angles of the power provided to the A and C electrodes by 132 degrees during that entire on period. During the immediately subsequent off period, the phase angles were again changed so that electrodes A and C would lead electrodes B and D.

The inventor hereby incorporates by reference U.S. Pat. Nos. 6,050,994 and 6,171,305.

While several particular forms of the invention have been illustrated and described, it will be apparent that various modifications can be made without departing from the spirit and scope of the invention. For example, the controller 20 is shown in FIG. 1 as forming a part of the power control system 12. However, it may take other forms such as an external processor in a separate computer for example. Likewise, duty cycle control and phase control may be performed by circuits other than those shown here.

Accordingly, it is not intended that the invention be limited, except as by the appended claims.

What is claimed is:

1. A system for delivering energy to a biological site, said system comprising:
   a catheter having a plurality of electrodes at its distal end and adapted to position at least two of the plurality of electrodes at the biological site;
   a backplate adapted to be positioned proximal the biological site so that the biological site is interposed between the electrode device and the backplate;
   a power generator adapted to provide power to each of the electrodes, the power having a duty cycle with an on period and an off period; and
   a processor adapted to control the provision of power to each of the electrodes such that:
      during a first segment of the on period, a voltage potential is established between at least one electrode and the backplate so that the energy flows through the biological site between the electrode and the backplate; and
      during a second segment of the on period, a voltage potential is established between a least two of the electrodes so that energy flows through the biological site between the electrodes.

2. The system of claim 1 wherein the processor is further adapted to adjust the duration of the first segment and second segment.

3. The system of claim 1 wherein, during the first segment, each electrode has substantially the same voltage level such that substantially no current flows between the electrodes.

4. The system of claim 1 wherein, during the second segment, the voltage potential between at least two electrodes is established by providing power to each of the electrodes having voltage levels that differ from each other.

5. The system of claim 4 wherein the processor is adapted to control the power generator to provide power with different phase angles to at least two of the electrodes.

6. The system of claim 5 wherein the power generator provides power that differs in phase by an amount greater than zero degrees but less than 180 degrees to at least two of the electrodes.

7. The system of claim 5 wherein the power generator provides power that differs in phase by approximately 132 degrees to at least two of the electrodes.

8. The system of claim 4 wherein the processor is adapted to control the power generator to provide power having different phase angles to adjacent electrodes.

9. The system of claim 4 wherein the processor is adapted to control the power generator to provide separate power to each of the plurality of electrodes and individually control the phase angle of the power to each electrode.

10. The system of claim 4 wherein the processor is adapted to control the power generator to provide separate power to each of the plurality of electrodes and individually control the duty cycle of the power to each electrode.

11. The system of claim 1 wherein, during the second segment, the voltage potential between at least two electrodes is established by connecting at least one electrode to a first potential and providing power to at least one of the electrodes having a voltage level different than the first potential.

12. The system of claim 1 wherein the processor is further adapted to, during the second segment:
   form the plurality of electrodes into a first electrode group and a second electrode group with at least one electrode in each group;
   connect all electrodes in the first group to a first potential; and
   apply power to all electrodes in the second group from the power generator with the power establishing a second potential different from the first potential at each of the electrodes in the second electrode group.

13. The system of claim 12 wherein the processor is further adapted to interspace the electrodes from the first group of electrodes with the electrodes of the second group of electrodes such that each electrode from the first group is adjacent at least one electrode from the second group.

14. The system of claim 12 wherein the electrodes are arranged into a linear array at the distal end of the catheter.

15. A power control system for delivering energy to a biological site interposed between a plurality of electrodes and a backplate, said power control system comprising:
   a power generator adapted to provide power to each of the electrodes, the power having a duty cycle with an on period and an off period; and
   a processor adapted to control the provision of power to each of the electrodes such :
      during a unipolar segment of the on period, a voltage potential is established between at least one electrode and the backplate so that energy flows through the biological site between the electrode and the backplate; and
      during a bipolar segment of the on period, a voltage potential is established between at least two of the electrodes so that energy flows through the biological site between the electrodes.

16. The power control system of claim 15 wherein the processor is further adapted to alternate between unipolar segments and bipolar segments within the on period of the duty cycle.

17. The power control system of claim 15 wherein the processor is further adapted to control the duration of the unipolar segment and bipolar segment within the on period.

18. An ablation system comprising:
   a catheter having a plurality of electrodes at its distal end;
   a backplate;
   a power generator adapted to maintain the backplate at a reference voltage and to provide power to each of the electrodes, the power having a duty cycle with an on period and an off period; and
   a processor adapted to control the provision of power to each of the electrodes such that:
      during a first segment of the on period, a voltage potential is established between at least one electrode and the backplate; and
      during a second segment of the on period, a voltage potential is established between at least two of the electrodes.

19. The system of claim 18 wherein the processor is further adapted to adjust the duration of the first segment and second segment.

20. The system of claim 18 wherein, during the first segment, each electrode has substantially the same voltage level such that substantially no current flows between the electrodes.

21. The system of claim 18 wherein, during the second segment, the voltage potential between at least two electrodes is established by providing power to each of the electrodes having voltage levels that differ from each other.

22. A system for delivering energy to a biological site, said system comprising:
   a catheter having a plurality of electrodes at its distal end and adapted to position at least two of the plurality of electrodes at the biological site;

a backplate adapted to be positioned proximal the biological site so that the biological site is interposed between the at least two electrodes and the backplate;

a power generator adapted to provide power to each of the electrodes; and a processor adapted to control the provision of power to each of the at least two electrodes such that:

during a first time segment of power provision to each of the at least two electrodes, a voltage potential is established between at least one electrode and the backplate so that energy flows through the biological site between the electrode and the backplate; and during a second time segment of power provision to each of the at least two electrodes, a voltage potential is established between the electrodes so that energy flows through the biological site between the electrodes.

23. The system of claim 22 wherein the processor is further adapted to adjust the duration of the first time segment and the second time segment.

24. The system of claim 22 wherein, during the first time segment, each electrode has substantially the same voltage level such that substantially no current flows between the electrodes.

25. The system of claim 22 wherein, during the second time segment, the voltage potential between at least two electrodes is established by providing power to each of the electrodes having voltage levels that differ from each other.

26. The system of claim 25 wherein the processor is adapted to control the power generator to provide power with different phase angles to the at least two of the electrodes.

27. The system of claim 25 wherein the processor is adapted to control the power generator to provide separate power to each of the plurality of electrodes and individually control the phase angle of the power to each electrode.

28. The system of claim 25 wherein the processor is adapted to control the power generator to provide separate power to each of the plurality of electrodes.

29. The system of claim 22 wherein, during the second time segment, the voltage potential between at least two electrodes is established by connecting at least one electrode to a first potential and providing power to at least one of the electrodes having a voltage level different than the first potential.

30. The system of claim 22 wherein the processor is further adapted to, during the second time segment:

form the plurality of electrodes into a first electrode group and a second electrode group with at least one electrode in each group;

connect all electrodes in the first group to a first potential; and apply power to all electrodes in the second group from the power generator with the power establishing a second potential different from the first potential at each of the electrodes in the second electrode group.

31. The system of claim 30 wherein the processor is further adapted to interspace the electrodes from the first group of electrodes with the electrodes of the second group of electrodes such that each electrode from the first group is adjacent at least one electrode from the second group.

32. A power control system for delivering energy to a biological site interposed between a plurality of electrodes and a backplate, said power control system comprising:

a power generator adapted to provide power to each of the electrodes; and a processor adapted to control the provision of power to each of the electrodes such that:

during a unipolar segment of power provision to at least two of the electrodes, a voltage potential is established between at least one electrode and the backplate so that energy flows through the biological site between the electrode and the backplate; and during a bipolar segment of power provision to at least two of the electrodes, a voltage potential is established between the electrodes so that energy flows through the biological site between the electrodes.

33. The power control system of claim 32 wherein the processor is further adapted to alternate between unipolar segments and bipolar segments.

34. The power control system of claim 32 wherein the processor is further adapted to control the duration of the unipolar segment and bipolar segment.

35. An ablation system comprising:

a catheter having a plurality of electrodes at its distal end;

a backplate;

a power generator adapted to maintain the backplate at a reference voltage and to provide power to each of the electrodes; and a processor adapted to control the provision of power to each of the electrodes such that:

during a first time segment of power provision to at least two of the electrodes, a voltage potential is established between at least one electrode and the backplate; and during a second time segment of power provision to at least two of the electrodes, a voltage potential is established between the electrodes.

36. The system of claim 35 wherein the processor is further adapted to adjust the duration of the first time segment and the second time segment.

37. The system of claim 35 wherein, during the first time segment, each electrode has substantially the same voltage level such that substantially no current flows between the electrodes.

38. The system of claim 35 wherein, during the second time segment, the voltage potential between at least two electrodes is established by providing power to each of the electrodes having voltage levels that differ from each other.

* * * * *

UNITED STATES PATENT AND TRADEMARK OFFICE
CERTIFICATE OF CORRECTION

PATENT NO. : 6,488,678 B1
DATED : December 3, 2002
INVENTOR(S) : Marshall L. Sherman It is certified that error appears in the above-identified patent and that said Letters Patent is hereby corrected as shown below:

Column 12,
Line 30, after "by:" add the following:

$$-- \; I_{e\text{-}b} = \frac{V \sin(2\pi ft)}{Z_{e\text{-}b}} \qquad (\text{Eq. 3}) \; --.$$

Line 41, after "by:" add the following:

$$-- \; \frac{I_{e\text{-}e}}{I_{e\text{-}b}} = 2\sin\left(\frac{\Delta\Phi}{2}\right) \qquad (\text{Eq. 4}) \; --.$$

Column 13,
Line 64, after "shown:" add the following

| Device | Part No. | Manufacturer |
|---|---|---|
| -- U1 | GAL6002B | Lattice |
| U2 | SN75372 | numerous |
| Q1 | 1RFZ34N | numerous |
| Q2, Q3, Q4, Q5 | 1RFZ44N | numerous |
| Q7, Q8, Q9 | MPF660l | numerous |
| R3, R5 | 1Ω | numerous |
| T1, T4 | CMI-4810 | Corona Magnetics, Inc. |
| T2 | GFS97-0131-1 | GFS Manufacturing |
| T5 | CMI-4809 | Corona Magnetics, Inc. -- |

Signed and Sealed this

Eighth Day of April, 2003

JAMES E. ROGAN
*Director of the United States Patent and Trademark Office*